(12) United States Patent
Zhao et al.

(10) Patent No.: US 8,971,597 B2
(45) Date of Patent: Mar. 3, 2015

(54) EFFICIENT VISION AND KINEMATIC DATA FUSION FOR ROBOTIC SURGICAL INSTRUMENTS AND OTHER APPLICATIONS

(75) Inventors: Tao Zhao, Sunnyvale, CA (US); Wenyi Zhao, Mountain View, CA (US); Brian D. Hoffman, Sunnyvale, CA (US); William C. Nowlin, Los Altos, CA (US); Hua Hui, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1270 days.

(21) Appl. No.: 12/495,304

(22) Filed: Jun. 30, 2009

(65) Prior Publication Data
US 2010/0331855 A1 Dec. 30, 2010

(51) Int. Cl.
*G06K 9/00* (2006.01)
*A61B 19/00* (2006.01)

(52) U.S. Cl.
CPC ..... *A61B 19/2203* (2013.01); *A61B 2019/5259* (2013.01); *A61B 2019/5265* (2013.01); *A61B 2019/5437* (2013.01)
USPC .............................................. 382/128; 606/1

(58) Field of Classification Search
CPC .... G06T 7/0012; G06T 7/0083; G06F 19/321
USPC .............................................. 606/1; 382/128
See application file for complete search history.

(56) References Cited

U.S. PATENT DOCUMENTS

| | | | |
|---|---|---|---|
| 4,219,842 A | 8/1980 | Miller | |
| 4,603,231 A | 7/1986 | Reiffel et al. | |
| 4,614,366 A | 9/1986 | North et al. | |
| 5,175,616 A | 12/1992 | Milgram et al. | |
| 5,217,003 A | 6/1993 | Wilk | |
| 5,428,192 A | 6/1995 | Chen et al. | |
| 5,432,528 A | 7/1995 | Ritter | |
| 5,457,754 A | 10/1995 | Han et al. | |
| 5,468,921 A | 11/1995 | Blake et al. | |
| 5,561,708 A | 10/1996 | Remillard | |

(Continued)

FOREIGN PATENT DOCUMENTS

| | | |
|---|---|---|
| EP | 1168246 A2 | 1/2002 |
| JP | 2005118232 A | 5/2005 |

(Continued)

OTHER PUBLICATIONS

U.S. Appl. No. 12/415,377, filed Mar. 21, 2009; first named inventor: Tao Zhao.

(Continued)

*Primary Examiner* — William Thomson
*Assistant Examiner* — John R Downey

(57) ABSTRACT

Robotic devices, systems, and methods for use in telesurgical therapies through minimally invasive apertures make use of joint-based data throughout much of the robotic kinematic chain, but selectively rely on information from an image capture device to determine location and orientation along the linkage adjacent a pivotal center at which a shaft of the robotic surgical tool enters the patient. A bias offset may be applied to a pose (including both an orientation and a location) at the pivotal center to enhance accuracy. The bias offset may be applied as a simple rigid transformation from the image-based pivotal center pose to a joint-based pivotal center pose.

32 Claims, 14 Drawing Sheets

(56) References Cited

U.S. PATENT DOCUMENTS

| | | | |
|---|---|---|---|
| 5,577,991 A | 11/1996 | Akui et al. | |
| 5,579,057 A | 11/1996 | Banker et al. | |
| 5,583,536 A | 12/1996 | Cahill, III | |
| 5,657,095 A | 8/1997 | Yoshida et al. | |
| 5,797,900 A | 8/1998 | Madhani et al. | |
| 5,808,665 A | 9/1998 | Green | |
| 5,836,869 A | 11/1998 | Kudo et al. | |
| 5,839,441 A | 11/1998 | Steinberg | |
| 5,855,583 A | 1/1999 | Wang et al. | |
| 5,950,629 A | 9/1999 | Taylor et al. | |
| 5,987,349 A | 11/1999 | Schulz | |
| 6,057,833 A | 5/2000 | Heidmann et al. | |
| 6,097,994 A | 8/2000 | Navab et al. | |
| 6,108,458 A | 8/2000 | Hart | |
| 6,122,541 A * | 9/2000 | Cosman et al. | 600/426 |
| 6,139,490 A | 10/2000 | Breidenthal et al. | |
| 6,159,016 A | 12/2000 | Lubell et al. | |
| 6,201,984 B1 | 3/2001 | Funda et al. | |
| 6,246,900 B1 * | 6/2001 | Cosman et al. | 600/426 |
| 6,424,885 B1 | 7/2002 | Niemeyer et al. | |
| 6,434,416 B1 | 8/2002 | Mizoguchi et al. | |
| 6,459,926 B1 | 10/2002 | Nowlin et al. | |
| 6,468,265 B1 | 10/2002 | Evans et al. | |
| 6,470,236 B2 | 10/2002 | Ohtsuki | |
| 6,484,049 B1 * | 11/2002 | Seeley et al. | 600/426 |
| 6,490,475 B1 * | 12/2002 | Seeley et al. | 600/426 |
| 6,493,608 B1 | 12/2002 | Niemeyer | |
| 6,522,906 B1 | 2/2003 | Salisbury, Jr. et al. | |
| 6,587,750 B2 | 7/2003 | Gerbi et al. | |
| 6,612,980 B2 | 9/2003 | Chen et al. | |
| 6,659,939 B2 | 12/2003 | Moll et al. | |
| 6,678,090 B2 | 1/2004 | Spink | |
| 6,714,839 B2 | 3/2004 | Salisbury, Jr. et al. | |
| 6,714,841 B1 | 3/2004 | Wright et al. | |
| 6,720,988 B1 | 4/2004 | Gere et al. | |
| 6,731,988 B1 | 5/2004 | Green | |
| 6,741,757 B1 | 5/2004 | Torr et al. | |
| 6,791,601 B1 | 9/2004 | Chang et al. | |
| 6,799,065 B1 | 9/2004 | Niemeyer | |
| 6,817,972 B2 | 11/2004 | Snow | |
| 6,837,883 B2 | 1/2005 | Moll et al. | |
| 6,839,456 B2 | 1/2005 | Touzawa et al. | |
| 6,856,324 B2 | 2/2005 | Sauer et al. | |
| 6,856,826 B2 * | 2/2005 | Seeley et al. | 600/426 |
| 6,856,827 B2 * | 2/2005 | Seeley et al. | 600/426 |
| 6,864,886 B1 | 3/2005 | Cavallaro et al. | |
| 6,866,671 B2 | 3/2005 | Tierney et al. | |
| 6,949,106 B2 | 9/2005 | Brock et al. | |
| 6,980,210 B1 | 12/2005 | Weiglhofer et al. | |
| 7,075,556 B1 | 7/2006 | Meier et al. | |
| 7,155,315 B2 | 12/2006 | Niemeyer et al. | |
| 7,194,118 B1 | 3/2007 | Harris et al. | |
| 7,277,120 B2 | 10/2007 | Gere et al. | |
| 7,689,014 B2 * | 3/2010 | Abovitz et al. | 382/128 |
| 7,907,166 B2 | 3/2011 | Lamprecht et al. | |
| 8,184,880 B2 | 5/2012 | Zhao et al. | |
| 8,218,727 B2 * | 7/2012 | Baumgart et al. | 378/98 |
| 8,423,182 B2 | 4/2013 | Robinson et al. | |
| 8,639,000 B2 | 1/2014 | Zhao et al. | |
| 8,830,224 B2 | 9/2014 | Zhao et al. | |
| 2002/0012460 A1 | 1/2002 | Kochi et al. | |
| 2002/0058929 A1 | 5/2002 | Green | |
| 2003/0151809 A1 | 8/2003 | Takahashi et al. | |
| 2003/0158463 A1 | 8/2003 | Julian et al. | |
| 2003/0210812 A1 | 11/2003 | Khamene et al. | |
| 2003/0216715 A1 | 11/2003 | Moll et al. | |
| 2004/0002642 A1 | 1/2004 | Dekel et al. | |
| 2004/0009459 A1 | 1/2004 | Anderson et al. | |
| 2004/0022418 A1 | 2/2004 | Oota | |
| 2004/0039485 A1 | 2/2004 | Niemeyer et al. | |
| 2004/0052333 A1 | 3/2004 | Sayre et al. | |
| 2004/0070615 A1 | 4/2004 | Ewing et al. | |
| 2004/0240725 A1 | 12/2004 | Xu et al. | |
| 2004/0263613 A1 | 12/2004 | Morita | |
| 2005/0054910 A1 * | 3/2005 | Tremblay et al. | 600/411 |
| 2005/0154288 A1 | 7/2005 | Wang et al. | |
| 2005/0179702 A1 | 8/2005 | Tomlinson et al. | |
| 2006/0013473 A1 | 1/2006 | Woodfill et al. | |
| 2006/0058919 A1 * | 3/2006 | Sommer | 700/245 |
| 2006/0087504 A1 | 4/2006 | Meier et al. | |
| 2006/0142657 A1 | 6/2006 | Quaid et al. | |
| 2006/0241414 A1 | 10/2006 | Nowlin et al. | |
| 2006/0258938 A1 | 11/2006 | Hoffman et al. | |
| 2007/0021738 A1 | 1/2007 | Hasser et al. | |
| 2007/0038080 A1 | 2/2007 | Salisbury, Jr. et al. | |
| 2007/0078334 A1 * | 4/2007 | Scully et al. | 600/424 |
| 2007/0138992 A1 * | 6/2007 | Prisco et al. | 318/568.21 |
| 2007/0147707 A1 | 6/2007 | Coste-Maniere et al. | |
| 2007/0156017 A1 | 7/2007 | Lamprecht et al. | |
| 2007/0161854 A1 * | 7/2007 | Alamaro et al. | 600/109 |
| 2007/0167702 A1 | 7/2007 | Hasser et al. | |
| 2007/0183041 A1 | 8/2007 | McCloy et al. | |
| 2007/0211927 A1 * | 9/2007 | Groszmann et al. | 382/128 |
| 2007/0265527 A1 | 11/2007 | Wohlgemuth | |
| 2008/0004603 A1 | 1/2008 | Larkin et al. | |
| 2008/0013809 A1 * | 1/2008 | Zhu et al. | 382/128 |
| 2008/0027356 A1 | 1/2008 | Chen et al. | |
| 2008/0033240 A1 | 2/2008 | Hoffman et al. | |
| 2008/0065109 A1 | 3/2008 | Larkin | |
| 2008/0125794 A1 | 5/2008 | Brock et al. | |
| 2008/0177284 A1 | 7/2008 | Lee et al. | |
| 2008/0285724 A1 | 11/2008 | Dehler | |
| 2009/0015004 A1 | 1/2009 | Long | |
| 2009/0036902 A1 | 2/2009 | DiMaio et al. | |
| 2009/0046146 A1 | 2/2009 | Hoyt | |
| 2009/0069821 A1 | 3/2009 | Farritor et al. | |
| 2009/0088634 A1 | 4/2009 | Zhao et al. | |
| 2009/0088773 A1 | 4/2009 | Zhao et al. | |
| 2009/0088897 A1 | 4/2009 | Zhao et al. | |
| 2009/0171332 A1 | 7/2009 | Bonneau | |
| 2009/0192523 A1 | 7/2009 | Larkin et al. | |
| 2009/0192524 A1 | 7/2009 | Itkowitz et al. | |
| 2009/0248036 A1 | 10/2009 | Hoffman et al. | |
| 2009/0248041 A1 | 10/2009 | Williams et al. | |
| 2009/0268010 A1 | 10/2009 | Zhao et al. | |
| 2009/0268011 A1 | 10/2009 | Scott et al. | |
| 2009/0268012 A1 | 10/2009 | Scott et al. | |
| 2009/0268015 A1 | 10/2009 | Scott et al. | |
| 2009/0270678 A1 | 10/2009 | Scott et al. | |
| 2009/0326553 A1 | 12/2009 | Mustufa et al. | |
| 2010/0169815 A1 | 7/2010 | Zhao et al. | |
| 2010/0204713 A1 | 8/2010 | Ruiz | |
| 2010/0228249 A1 | 9/2010 | Mohr et al. | |
| 2011/0050852 A1 | 3/2011 | Lamprecht et al. | |

FOREIGN PATENT DOCUMENTS

| | | |
|---|---|---|
| JP | 2008245838 A | 10/2008 |
| WO | WO-0129681 A1 | 4/2001 |
| WO | WO-0229723 A1 | 4/2002 |
| WO | WO-0345222 A2 | 6/2003 |
| WO | WO-2004029786 A1 | 4/2004 |
| WO | WO-2005037093 A1 | 4/2005 |
| WO | WO-2005102202 A1 | 11/2005 |
| WO | WO-2005119505 A2 | 12/2005 |
| WO | WO-2006124388 A1 | 11/2006 |
| WO | WO-2006131373 A2 | 12/2006 |
| WO | WO-2007120351 A2 | 10/2007 |
| WO | WO-2008079546 A2 | 7/2008 |
| WO | WO-2009025783 A1 | 2/2009 |
| WO | WO-2009045827 A2 | 4/2009 |
| WO | WO-2009085616 A1 | 7/2009 |

OTHER PUBLICATIONS

U.S. Appl. No. 12/428,657, filed Apr. 23, 2009; ; first named inventor: Tao Zhao.

U.S. Appl. No. 12/428,691, filed Apr. 23, 2009; ; first named inventor: Tao Zhao.

U.S. Appl. No. 12/465,020, filed May 13, 2009; first named inventor: Wenyi Zhao.

U.S. Appl. No. 12/465,029, filed May 13, 2009; first named inventor: Wenyi Zhao.

(56) References Cited

OTHER PUBLICATIONS

U.S. Appl. No. 12/485,503, filed Jun. 16, 2009; first named inventor: Brandon D. Itkowitz.
U.S. Appl. No. 12/485,545, filed Jun. 16, 2009; first named inventor: Brandon D. Itkowitz.
U.S. Appl. No. 61/203,975, filed Dec. 31, 2008; first named inventor: Tao Zhao.
U.S. Appl. No. 61/204,082, filed Dec. 31, 2008; first named inventor: Wenyi Zhao.
Fischler et al., "Random sample consensus: a paradigm for model fitting with applications to image analysis and automated cartography," Communications of the ACM, vol. 24, No. 6, Jun. 1981, pp. 381-395.
Kim, Miriam et al., "Computer Assisted 3D Measurements for Micro-Surgery," Proceedings of the Human Factors and Ergonomics Society 41st Annual Meeting, 1997, pp. 787-791, Human Factors and Ergonomics Society.
Kosaka, Akio et al., "Augmented Reality System for Surgical Navigation Using Robust Target Vision," IEEE Conference on Computer Vision and Pattern Recognition, 2000, vol. 2, pp. 187-194.
Lowe, David G., "Distinctive Image Features from Scale-Invariant Keypoints," International Journal of Computer Vision, vol. 60, No. 2, Nov. 2004, pp. 91-110.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Vertut, Jean and Phillipe Coiffet, "Robot Technology: Teleoperation and Robotics Evolution and Development—vol. 3A", English translation Prentice-Hall, Inc., Inglewood Cliffs, NJ, USA 1986, vol. 3A, 332 pages.
Anderson B.L., "Stereovision: Beyond Disparity Computation," Trends in Cognitive Sciences, 1998, vol. 2 (6), pp. 214-222.
Ayala, Hugo M, et al., "Wear of Oil Containment Elastomer in Abrasive Slurries," 1998, pp. 9-21, vol. 220—Issue. 1, Elsevier Science.
Barron, J.L. et al., "Performance of optical flow techniques," Intl. J. of Computer Vision, 1994, pp. 43-77, vol. 12—Issue. 1.
Benson, K. Blair, "Television Engineering Handbook," 1986, pp. 14.68-14.72, McGraw-Hill.
Boeckeler Instruments, Inc., "Pointmaker PVI-44 Compact Video Marker Manual," Section One, 2006, pp. 3-32.
Boeckeler Instruments, Inc., "Pointmaker PVI-X90 Presentation System," specification sheet, www.pointmaker.com, ©1994-2004, 2 pages.
Brown, Myron M. et al., "Advances in Computational Stereo," IEEE Transactions on Pattern Analysis and Machine Intelligence (PAMI), 2003, pp. 993-1008, vol. 25 Issue, IEEE.
Carter, William, "The advantage of single lens stereopsis," Stereoscopic Displays and Applications III, 1992, pp. 204-210, vol. 1669, SPIE.
FR0611491 Preliminary Search Report, mailed Mar. 26, 2010, 6 pages.
Guthart, Gary S. et al., "The IntuitiveT telesurgery system: overview and application," Proceedings of the 2000 IEEE International Conference on Robotics & Automation, 2000, pp. 618-621, vol. 1, IEEE.
Hart, Douglas P., "Second-Order Correlation," YAYOI Symposium on Particle Imaging Velocimetry (VSJ-SPIE98 Post-Conference Symposium), 1998, 14 pages.
Hart, Douglas P., "High speed PIV analysis using compressed image correlation," Journal of Fluids Engineering, 1998, pp. 463-470, vol. 120.
Hart, Douglas P., "Sparse array image correlation," 8th International Symposium on Applications of Laser Techniques to Fluid Mechanics, 1996, pp. 53-74, vol. 1 (Session 1).
Hart, Douglas P., "PIV Error Correction," 9th International Symposium on Applications of Laser Techniques to Fluid Mechanics, Jul. 13-16, 1998, Lisbon, Portugal, in Laser Techniques Applied to Fluid Mechanics: Selected Papers from the 9th International Symposium, 1998, pp. 19-36.
Hart, Douglas P., "PIV error correction," Experiments in Fluids, 2000, pp. 13-22, vol. 29—Issue 1, Springer-Verlag.
Hart, Douglas P., "Successive Approximation PIV Analysis to Achieve High Accuracy," Resolution, and Speed, The 13th U.S. National Congress of Applied Mechanics, 1998, 1 page.
Hart, Douglas P., "Super-Resolution PIV Processing by Recursive Correlation," Journal of Visualization,The Visualization Society of Japan, 2000, pp. 187-194, vol. 10.
Hidrovo, Carlos H. et al., "2-D thickness and Temperature Mapping of Fluids by Means of Two Dye Laser Induced Fluorescence Ratiometric Scheme," Proceedings of the 3rd Pacific Symposium on Flow Visualization and Image Processing, 2001, 30 pages.
Hidrovo, Carlos H. et al., "2-D thickness and Temperature Mapping of Fluids by Means of Two-Dye Laser Induced Fluorescence Ratiometric Scheme," Journal of Flow Visualization and Image Processing, 2002, pp. 171-191, vol. 9.
Hidrovo, Carlos H. et al., "Emission Reabsorption Laser Induced Fluorescence for Film Thickness Measurement," Measurement Science and Technology, 2001, pp. 467-477, vol. 12—Issue 4, Institute of Physics Publishing.
Horn, Berthold K.P. et al., "Determining Optical Flow, Artificial Intelligence," 1981, pp. 185-203, vol. 17.
Huang, Hayden et al., "Quantified flow Characteristics in a Model Cardiac Assist Device," Measurement and Instrumentation Forum, ASME Fluids Engineering Division Summer Meeting, Jun. 22-26, 1997, 6 pages.
Jojic, Nebojsa et al., "Tracking Self-Occluding Articulated Objects in Dense Disparity Maps," IEEE International Conference on Computer Vision, Corfu, 1999, pp. 123-130, vol. 1, IEEE.
Kavoussi, Louis R. et al., "Telerobotic Assisted Laparoscopic Surgery: Initial Laboratory and Clinical Experience," Urology, Jul. 1994, pp. 15-19, vol. 44—Issue 1.
Keith, Jack, ideo Demystified, A Handbook for the Engineer, 1993, pp. 338-356, HighText Publications, Inc., Solana Beach, CA, USA, ISBN: 1-878707-09-4.
Keramas, James G., "Robot Technology Fundamentals," 1999, pp. 193-219.
Kim, Yoon Sang, "Surgical Telementoring Initiation of a Regional Telemedicine Network: Projection of Surgical Expertise in the WWAMI Region," 3rd 2008 International Conference on Convergence and Hybrid Information Technology (ICCIT 08), Nov. 11-13, 2008, Busan, Korea, vol. 1, pp. 974-979, IEEE.
Lammerding, J. et al., "Monocular 3-D Magnetic Bead Microrheometry," 11th International Symposium on Application of Laser Techniques to Fluid Mechanics, 2002, 4 pages.
Lin, Cheng-Hsien et al., "Ultrasound motion estimation using a hierarchical feature weighting algorithm," Computerized Medical Imaging and Graphics, 2007, vol. 31, pp. 178-190, Elsevier.
Link, Richard E. et al., "Telesurgery: Remote Monitoring and Assistance During Laparoscopy," Urol Clin North Am, 2001, pp. 177-188, vol. 28—Issue 1, Sanders.
Micali, S. et al., "Feasibility of telementoring between Baltimore (USA) and Rome (Italy): the first five cases," J Endourol, 2000, pp. 493-496, vol. 14—Issue 6.
Moore, R.G. et al., "Telementoring of laparoscopic procedures: Initial clinical experience," Surgical Endoscopy, 1996, pp. 107-110, vol. 10—Issue 2, Springer-Verlag.
Official Action mailed Aug. 8, 2012 for JP Application No. 2006335952 filed Dec. 13, 2006.
PCT/US06/62381 International Search Report, mailed Jan. 2, 2008, 1 page.
PCT/US06/62381 Written Opinion of the International Search Authority, mailed Jan. 2, 2008, 6 pages.
PCT/US09/68427 International Search Report and Written Opinion of the International Searching Authority, mailed Nov. 23, 2010, 20 pages.
PCT/US09/68427 Partial International Search Report, mailed Jun. 18, 2010, 6 pages.

(56) References Cited

OTHER PUBLICATIONS

PCT/US10/35402 International Search Report and Written Opinion of the International Searching Authority, mailed Aug. 2, 2010, 16 pages.

PCT/US10/37293 International Search Report and Written Opinion of the International Searching Authority, mailed Nov. 29, 2010, 19 pages.

Rafiq A., et al., "Digital Video Capture and Synchronous Consultation in Open Surgery," Annals of Surgery, 2004, vol. 239 (4), pp. 567-573.

Rafiq, Azhar et al., "SOCRATES:" Telementoring for Telerobotics, and Todd Drasin et al., "Using Telerobots as Assistant Surgeons," Chapters 11 and 26: Primer of Robotic & Telerobotic Surgery, Garth H. Ballentyne et al., 2004, Ilppincott Williams & Wilkins, pp. 78-85 and 188-195.

Rohaly, Janos et al., "High Resolution Ultrafast 3D Imaging," Proceedings of Photonics West 2000: Three Dimensional Image Capture and Application III, 2000, pp. 2-10, vol. 3958, SPIE.

Rohaly, Janos et al., "Monocular 3-D Active Micro-PTV," 4th International Symposium on Particle Image Velocimetry, 2001, pp. 1-4, paper No. 1147.

Rohaly, Janos et al., "Reverse Hierarchical PIV Processing," 4th International Symposium on Particle Image Velocimetry, 2001, 16 pages, paper No. 1009.

Saga, Sato et al., "A Method for Modeling Freehand Curves-the Fuzzy Spline Interpolation," Systems and Computers in Japan, Sep. 26, 1995, vol. 26, Issue 10, pp. 77-87, Scripta Technica, Inc.

Scharstein D., et al., A Taxonomy and Evaluation of Dense Two-Frame Stereo Correspondence Algorithm, Proceedings of the IEEE Workshop on Stereo and Multi-Baseline Vision, 2001, 10 pages.

Schulam Peter G. et al., "Telesurgical mentoring: Initial clinical Experience," Surgical Endoscopy, 1997, pp. 1001-1005, vol. 11, Springer-Verlag.

See, William A. et al., "Predictors of laparoscopic complications after formal training in laparoscopic surgery," Journal of the American Medical Association, 1993, pp. 2689-2692, vol. 270—Issue 22.

Stefano L.D., et al., "A Fast Area-Based Stereo Matching Algorithm," Image and Vision Computing, 2004, vol. 22, pp. 983-1005.

Stoianovici, Dan, "Robotic tools for minimally invasive urologic surgery," Chapter in Complications of Urologic Laparoscopic Surgery: Recognition, Management and Prevention, published 2005 by Taylor Francis, paper dated Dec. 2002, 17 pages.

Thirouard, Benoist et al., "Investigation of Oil Transport Mechanisms in the Piston Ring Pack of a Single Cylinder Diesel Engine," Using Two-Dimensional Laser-Induced Fluorescence, SAE Transactions: Journal of Fuels and Lubricants, 1998, pp. 2007-2015, vol. 107—Issue 4.

Trucco, E. et al., "Real-Time Disparity Maps for Immersive 3-D Teleconferencing by Hybrid Recursive Matching and Census Transform," Dept. of Computing and Electrical Engineering, 2001, 9 pages.

Tzovaras, Dimitrios et al., "Disparity field and depth map coding for multiview 3D image generation," Signal Processing: Image Communication, 1998, pp. 205-230, vol. 11, Elsevier.

Wu, Chun-Hong et al., "Depth Mapping of Integral Images through Viewpoint Image Extraction with a Hybrid Disparity Analysis Algorithm," Journal of Display Technology, Mar. 2008, vol. 4, Issue No. 1, pp. 101-108, IEEE.

Office Action mailed Dec. 12, 2013 for Japanese Application 2012516111 filed Jun. 3, 2010.

Office Action mailed Dec. 20, 2013 for Chinese Application 201080027164.3 filed Jun. 3, 2010.

Lee, Benjamin R. et al., "A novel method of surgical instruction: international telementoring," World Journal of Urology, 1998, pp. 367-370, vol. 16—Issue 6, Springer Berlin / Heidelberg.

Lee C.H., et al., "Purification and Characterization of a Polysome-associated Endoribonuclease that Degrades c-myc mRNA in Vitro," The Journal of Biological Chemistry, 1998, vol. 273 (39), pp. 25261-25271.

* cited by examiner

EFFICIENT VISION AND KINEMATIC DATA FUSION FOR ROBOTIC SURGICAL INSTRUMENTS AND OTHER APPLICATIONS

CROSS-REFERENCES TO RELATED APPLICATIONS

The present application is related to U.S. patent application Ser. No. 12/428,657 filed on Apr. 23, 2009, entitled "Fiducial Marker Design And Detection For Locating Surgical Instruments In Images"; U.S. patent application Ser. No. 12/428,691 filed on Apr. 23, 2009, entitled "Configuration Marker Design And Detection For Instrument Tracking"; U.S. patent application Ser. No. 12/415,354 filed on Mar. 31, 2009, entitled "Synthetic Representation Of A Surgical Robot"; U.S. patent application Ser. No. 12/485,503 filed on Jun. 16, 2009, entitled "Virtual Measurement Tool For Minimally Invasive Surgery" U.S. patent application Ser. No. 11/130,471 filed on May 16, 2005, entitled "Methods and System for Performing 3-D Tool Tracking By Fusion of Sensor and/or Camera Derived Data During Minimally Invasive Robotic Surgery"; U.S. patent application Ser. No. 11/865,016 filed on Sep. 30, 2007 entitled "Tool Tracking Systems and Methods for Image Guided Surgery"; U.S. patent application Ser. No. 11/865,015 filed on Sep. 30, 2007, entitled "Methods of Locating and Tracking Robotic Instruments in Robotic Surgical Systems"; and U.S. patent application Ser. No. 11/865,014 filed on Sep. 30, 2007, entitled "Methods and Systems for Robotic Instrument Tool Tracking"; the full disclosures of which are incorporated herein by reference.

BACKGROUND

The present invention is generally related to improved robotic and/or surgical devices, systems, and methods. An exemplary embodiment provides a robotic surgical system which makes use of joint angles and/or positions along a robotic linkage to determine manipulator movement commands, and which selectively makes use of image processing data to correct a pivotal center through which the linkage extends into a patient body.

Minimally-invasive surgical techniques are aimed at reducing the amount of extraneous tissue that is damaged during diagnostic or surgical procedures, thereby reducing patient recovery time, discomfort, and collateral tissue damage. As a consequence, the average length of a hospital stay for standard surgery may be shortened significantly using minimally-invasive surgical techniques. Also, patient recovery times, patient discomfort, surgical side effects, and time away from work may also be reduced with minimally-invasive surgery.

Endoscopy is a well known form of minimally-invasive surgery, and a common form of endoscopy is laparoscopy, which is minimally-invasive inspection and surgery inside the abdominal cavity. In standard laparoscopic surgery, a patient's abdomen is insufflated with gas and cannula sleeves are passed through small (approximately ½ inch or less) incisions to provide entry ports for laparoscopic instruments.

Laparoscopic surgical instruments generally include a laparoscope or an endoscope (for viewing the surgical field), and working tools. The working tools are similar to those used in conventional open surgery, except that the working end or end effector of each tool is separated from its handle by an elongate shaft. The end effector or working part of the surgical instrument can manipulate or treat tissue, and may (for example) include clamps, graspers, scissors, staplers, image capture lenses, or needle holders.

To perform surgical procedures, the surgeon passes the working tools or instruments through cannula sleeves to an internal surgical site and manipulates them from outside the abdomen. The surgeon views the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

Minimally-invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a control console. While viewing a three-dimensional image of the surgical site on a suitable viewer or display, the surgeon performs the surgical procedures on the patient by manipulating master input or control devices of the control console. Each of the master input devices controls the motion of a servomechanically operated surgical instrument. During the surgical procedure, the telesurgical system can provide mechanical actuation and control of a variety of surgical instruments or tools having end effectors that perform various functions for the surgeon, e.g., holding or driving a needle, grasping a blood vessel, dissecting tissue, or the like, in response to manipulation of the master input devices.

While the new telesurgical robotic systems have tremendous promise for extending the capabilities of surgeons to perform therapies with less trauma to the patient, as with many successes, still further improvements would be desirable. For example, known robotic systems often rely on joint position information from sensors associated with each of the joints of a robotic linkage to calculate new end effector movement commands. While such joint-based information provides quite accurate relative movements of the end effector, the correlation between the absolute location and orientation of the end effector determined from this joint-based data may not precisely match the image of the end effector shown to the surgeon at the control console. Hence, a variety of potential enhancements to robotic surgery may benefit from more precise information regarding the actual tool locations, orientations, and movements. Although there have been proposals to enhance the accuracy of joint data using image-based information acquired from the endoscope of the telesurgical system, fusing the joint-based and image-based data can be computationally challenging.

In light of the above, it would be desirable to provide improved robotic systems for surgery and other applications. It would be particularly advantageous if the improvements enhanced the accuracy and precision of the tool position and/or orientation data available for use with the new robotic telesurgical systems for minimally invasive and other surgical procedures, ideally without requiring extensive additional computations or greatly increasing the complexity and cost of these advantageous systems.

BRIEF SUMMARY

The present invention generally provides improved robotic devices, systems, and methods, particularly for use in telesurgical therapies through minimally invasive apertures such as endoscopic cannula sleeves, a natural orifice, or the like. Embodiments of the invention may make use of joint-based data throughout much of the robotic kinematic chain, but may selectively rely on information from an image capture device (such as an endoscope or the like). This image-based data may be used to correct or define a pivotal center at which a shaft of the robotic surgical tool enters the patient. More specifically, robotic surgical tools (like known endoscopic tools) may have elongate shafts which pivot at a pivot point adjacent the aperture into the patient. Rather than attempting to recalculate or adjust joint data along the entire kinematic chain of the tool, based on an image, applying a simple and relatively stable adjustment or bias offset to an orientation along the shaft and the location at the pivotal center may significantly enhance the overall accuracy with which tool movements can be tracked. The shaft orientation and pivotal center location can define a remote center pose which is useful for these calculations. Advantageously, the bias offset may be applied as a simple rigid transformation from the image-based pivotal center pose to a joint-based pivotal center pose. This simple change may effectively replace the joint-based remote center pose with an image-based remote center pose within a processor module that tracks an end effector, calculates robotic movement commands of a tool or manipulator supporting the tool, calculates end effector movement distances, super imposes graphical overlays on the tool images, or the like. Advantageously, the system can gain much more accurate information recording the end effector without having to rigorously calculate a general solution of the tool kinematic chain based on the combination of the joint data and image data, thereby saving computational time and resources while accurately adjusting for much of the environmental constraints mechanically imposed on the system. Alternative embodiments may identify stationary or variable errors of other joints or linkages in the kinematic chain. A variety of enhancements to robotic surgery (including displaying of graphical overlays collocated with images of the physical tools, enhanced three dimensional measurements obtained robotically using the tools, collision detection, and the like) may benefit from the enhancements in pose information precision available with the methods and systems described herein.

In a first aspect, the invention provides a robotic method for performing surgery on a patient through a minimally invasive aperture. The method comprises positioning an elongate shaft of a tool through the aperture so that the shaft pivots at an actual pivot center adjacent the aperture. An image of the tool is acquired within the patient, and image-based pivotal center correction information is determined using the image. A position and/or orientation of the tool is determined by imposing the image-based pivotal center correction information onto joint-based data. The joint-based data is used by a robotic command module to calculate movements of a tool manipulator supporting the tool.

The calculations performed in determining and imposing the pivotal center correction information will typically be performed by a processor system of a robotic surgical system. The processor system will typically include the robotic command module which calculates the movement of a manipulator movably supporting the tool. Inputs to the command module typically include both a movement command (input from a surgeon or other system user) and the joint-based data (which may include joint position or speed as identified from potentiometers, encoders, or the like coupled to associated joints of the kinematic chain of the manipulator tool, and the like). The processor system will also often include a tool correction module which identifies the correction information to be applied to the joint-based data to provide more accurate tool position and/or orientation information than may be available from the joint-based data alone. The image-based pivotal center correction information may be determined by calculating a bias offset between a joint-based location of the pivotal center per the joint data from the manipulator and an image-based location of the pivotal center per the image. The position and/or orientation of the tool are determined by adjusting the joint-based pivotal center location per the bias offset such that the image-based pivotal center location substantially replaces the joint-based pivotal center location.

Typically, the bias offset will be calculated so as to include both location and orientation, such that the bias offset will comprise a pose bias offset. The joint-based pivotal center pose may be defined by the joint-based location of the pivotal center and an orientation of the shaft per joint data from the manipulator. An image-based pivotal center pose may be defined by the image-based pivotal center location and an orientation of the shaft per the image. The position and orientation of the tool are determined by adjusting the joint-based pivotal center pose per the bias offset such that the image-based pivotal center pose substantially replaces the joint-based pivotal center pose. Nonetheless, the poses along the linkages of the tool manipulator can be calculated using joint-based data. The pose or poses need not be calculated from a single image acquired at a single time, and will often be calculated using a time-series of images. When there is insufficient information in the image or images from a single time to fully determine the remote center pose, joint-based data synchronized with each image facilitates the correction of the image based pivotal center pose using sequential images. The process can be made more robust, particularly when a series of tool locations are obtained from the images, by identifying at least one of the calculated tool locations as being an outlier, and removing the at least one outlier before computing the image based pivotal center pose. More efficient tool location identification may be provided by determining a region of interest within the image based on one or more prior image-based tool locations, a tool trajectory, the joint based data, and/or the like.

The offset can be determined by calculating a simple rigid transformation between the joint-based pivotal center pose and the image-based pivotal center pose. The command module can apply the rigid transformation to the joint-based pivotal center pose using very little computation time and/or bandwidth. This surprisingly simple approach can significantly enhance the accuracy with which, for example, the surgical end effector and tool is tracked or (if used to calculate robotic movement commands) displayed to the surgeon and superimposed over the input master device in a telesurgical system.

The image is typically acquired by an image capture device that is movably supported by a camera manipulator. Suitable image capture devices may include, for example, optical or electronic endoscopes, remote imaging systems such as ultrasound transducers, fluoroscopy systems, magnetic resonance imaging (MRI) systems, or the like. The image-based pivotal center pose may be determined per a coordinate system of the image capture device. The command module may generate the joint-based pivotal center pose in response to joint states of the tool and the tool manipulator, and may similarly determine a joint-based camera coordinate system from joint data provided by the camera manipulator. The bias offset may be calculated between the joint-based pivotal center in the joint-based camera coordinate system, and the image-based pivotal center location in the camera coordinate system. This may effectively adjust for inaccuracies along the entire kinematic chain coupling the camera to the tool. For example, the camera manipulator may be supported by a movable camera support (such as a passive setup linkage that can be locked in position during surgery). The tool manipulator may similarly be supported by a movable tool support. The tool manipulator may pivot the shaft during the movements of the end effector about two axes that intersect at the pivotal center, with the two axes being referred to as a pitch axis and a yaw axis. Similarly, the image capture device may include an elongate shaft which is pivoted by the camera manipulator at a camera pivotal center about a camera pitch axis and a camera yaw axis. The bias offset may primarily comprise a combination of tool support data error, camera support data error, pitch data error, and yaw data error. The tool and camera support error may primarily result from inaccuracies in zeroing of the potentiometers or other joint sensors, structural inaccuracies (such as errors in the lengths of linkages, deflection of the links, or the like) of the kinematic linkages, particularly those of passive setup linkages which support the tool and/or camera manipulators.

In many embodiments, a plurality of images will be obtained by angularly offset image capture devices, such as through the use of a stereoendoscope or the like. This may facilitate determining a three-dimensional image-based pivotal center pose. The command module may determine joint-based pivotal center pose using joint data from the tool manipulator, and the image-based pivotal center pose may be determined using pairs of images from the image capture devices. The tool position and/or orientation may be determined by solving for a rigid transformation between the image-based pivotal center pose and the joint-based pivotal center pose using a recursive filter. The image-based pivotal center pose may be determined by identifying a plurality of marker points along the tool from the images. Alternatively (or in addition) the image-based pivotal center pose may be determined by identifying at least one structural location line along the tool from the images, such as an edge of the tool shaft.

In another aspect, the invention provides a robotic for performing surgery on a patient through a minimally invasive aperture with a robotic system. The robotic system includes a tool having an elongate shaft and a command module that determines movements of a tool manipulator supporting the tool by determining a joint-based pivotal center pose of the tool. The method comprises positioning the elongate shaft of the tool through the aperture so that the shaft pivots at an actual pivotal center adjacent to the aperture. The actual pivotal center and the shaft define an actual pivotal center pose. An image of the tool is acquired within the patient. An image-based pivotal center pose of the tool is determined using the image. A rigid transformation is calculated between the image-based pivotal center pose and the joint-based pivotal center pose using a recursive filter. A location and/or orientation of the tool is determined using the rigid transformation so as to mitigate an error between the joint-based pivotal center pose and the actual pivotal center pose.

In another aspect, the invention provides a robotic method for use with a robotic system. The robotic system includes a manipulator movably supporting a tool and a command module that generates movement commands of the manipulator so as to generate desired movements of the tool. The movement commands are generated based on joint data from the manipulator. Environmental constraints induce an error in a joint-based pose calculated by the command manipulator on a linkage of the manipulator or tool. The method comprises acquiring an image of the tool and/or manipulator. An image-based pose is selectively determined from the image. The pose reflects the environmental constraint. A rigid transformation is calculated between the image-based pose and the joint-based calculated pose. A pose of the tool is determined by using the rigid transformation so as to mitigate the error.

Advantageously, calculating and/or updating the rigid transformation may take a computation time which is less than one tenth, often being less than one one hundredth, and in many cases being less than one one thousandth or less than one ten thousandth of a computation time involved in determining a general solution for poses all along the manipulator linkage based on the image. Such general solutions often involve determining the inverse of large matrices, and by avoiding the need for such matrix inversion the robotic methods described herein may significantly enhance performance and/or conserve computational resources.

In another aspect, the invention provides a robotic system for performing surgery on a patient through a minimally invasive aperture. The system comprises a tool having an elongate shaft with a proximal end and a distal end. The distal end of the tool is insertable through the aperture so that the shaft pivots at a pivotal center adjacent the aperture. An image capture device acquires an image of the tool within the patient. A tool manipulator supports the proximal end of the tool, and a processor system couples the image capture device to the tool manipulator. The processor system includes a tool correction module and a robotic command module. The robotic command module is coupled to the tool manipulator so as to transmit tool movement commands thereto. The robotic command module also calculates a joint-based pivotal center in response to joint signals from the tool manipulator. The tool correction module generates a corrected tool position and/or orientation by determining image-based pivotal center correction information from the image, and by selectively correcting the joint-based pivotal center with the image-based pivotal center correction information.

In another aspect, the invention provides a correction system for use with a robotic surgical system. The robotic surgical system includes a tool having an elongate shaft with a distal end insertable through a minimally invasive aperture such that the shaft pivots at an actual pivotal center adjacent the aperture. The image capture device acquires an image of the tool within the patient, and a tool manipulator supports the tool. A robotic command module transmits movement commands to the tool manipulator, and also calculates joint-based pivotal center. The correction system comprises a tool correction module that couples the image capture device to the command module. The correction module determines a position and/or orientation of the tool by revising the joint-based pivotal center with image-based pivotal center correction information that is derived in response to the image of the tool within the patient. As a result, the tool correction module mitigates an error between the joint-based pivotal center and the actual pivotal center.

The tool correction module may be configured to determine and apply a bias offset between a joint-based location of the pivotal center per the joint signals, and an image-based location of the pivotal center. Similarly, the tool correction module may also determine a bias offset between a joint-based pivotal center pose (including the joint-based location and an orientation of the shaft per the joint signals) and an image-based pivotal center pose (defined by the image-based pivotal center location and an orientation of the shaft per the image). The offset may be determined by calculating rigid transformation between the joint-based pivotal center pose and the image-based pivotal center pose.

In yet another aspect, the invention provides a robotic system comprising a manipulator movably supporting a tool. A command module generates movement commands of the manipulator so as to generate desired movements of the tool based on joint data from the manipulator. Environmental constraints induce an error in a joint-based pose calculated by the command manipulator along the linkage of the manipulator or tool. An image capture device acquires an image of the tool and/or manipulator. Means for image-based correction couple the image capture device to the command module. The correction means comprises means for determining an image-based pose of the manipulator or tool from the image. The pose reflects the environmental constraints. Means for calculating a rigid transformation between the image-based pose and the joint-based calculated pose are also included in the means for correction, as well as means for using the rigid transformation to mitigate the error for determining a position and/or orientation of the tool.

In some embodiments, the command module may not apply the image-based pose for calculating the movement commands. Alternatively the embodiments may include a command module having means for applying the rigid transformation to calculate the movement commands.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
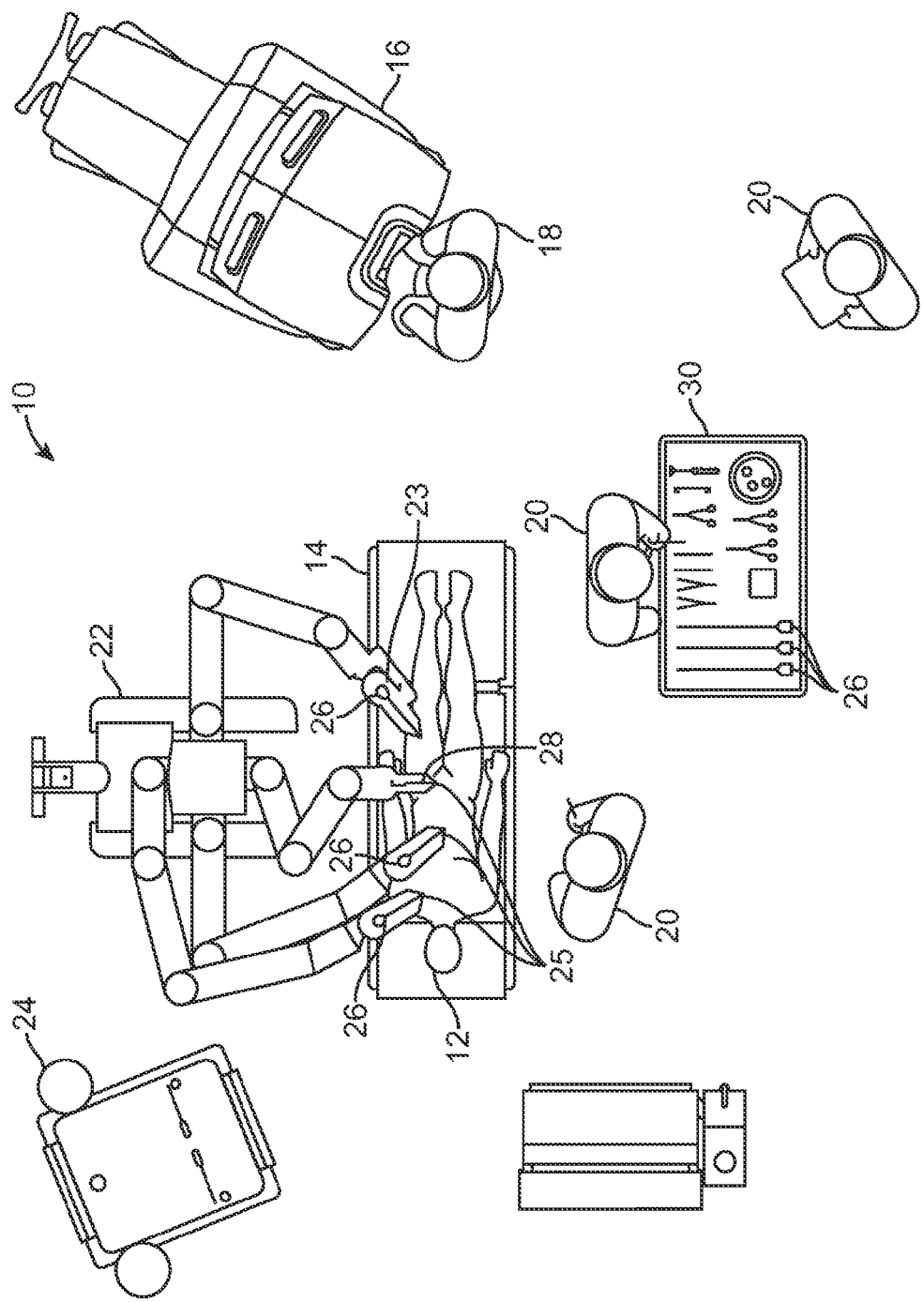
FIG. 1 is a plan view of a minimally-invasive robotic surgery system being used to perform a surgery, in accordance with embodiments of the invention.

The present invention generally provides improved robotic surgical devices, systems, and methods, particularly for telesurgery and other medical robotic applications. Embodiments of the present invention will find their most immediate use for correcting pose information (including position and/or orientation) of robotic surgical tools inserted through minimally invasive apertures to an internal surgical site. While existing robotic telesurgical systems do a good job of establishing and maintaining correspondence between movement of the master input device and movement of the end effector at an internal surgical site (as displayed to the surgeon), still further advantages may be obtained by providing more accurate information regarding the position and/or orientation of the tool (including the end effector, an elongate shaft of the tool extending through a minimally invasive aperture, linkages coupling the shaft to the end effector, and the like).

While robotic surgical applications through minimally invasive apertures may be the most immediate application, aspects of the invention may also find uses in other robotic fields and/or image analysis settings, particularly those in which environmental constraints can significantly alter an actual position or orientation of the machine driven structure away from a calculated pose using joint data or the like.

The calculations described herein for combining or fusing joint-based data (sometimes referred to as kinematic data) with image-based data will typically be performed by a processor system of the robotic surgical system. The processor system will typically include a robotic command module which calculates the movement of the tool. The movements will often be calculated in response to a movement command input by a surgeon or other system user, with the calculations applying the joint-based data (with the joint-based data often including joint position or speed information as identified from potentiometers, encoders, or the like that are coupled to associated passive or actively driven joints of the kinematic chain of the tool). The processor system will also often include a tool correction module which identifies a correction to be applied to the joint-based data to provide more accurate tool position and/or orientation information than may be available from the joint-based data alone, with the correction factor typically being calculated from images of the tool in a surgical workspace. Each of these modules may comprise data processing hardware and/or software, with the modules typically including one or more tangible medium embodying computer programming or code for performing the associated calculations. While the code of the robotic command module may run on the same processor board or boards as the code of the tool correction module, the exemplary embodiments employ different processor structures for calculating robotic movement command signals than those used for fusing the joint-based or kinematic data with the image based data. Similarly, while at least some joint-based data will typically be provided from the robotic command module to the tool correction module to perform the fusion between the joint-based data and the image-based data, in the exemplary embodiments the corrected pose information from the tool correction module is not employed by the robotic command module for use in calculating tool movements or the like. Other embodiments can apply the pose corrections for such purposes. Nonetheless, the most immediate application of the tool pose correction information from the tool correction module may be for superimposing graphical overlays on the moving tools in the display shown the system user, for facilitating enhanced three dimensional measurements obtained robotically using the robotic tools, for tool and/or manipulator collision detection and avoidance, for indicating positions of tools that are not visible in the system user display, for displaying tool activation or energizing icons, for graphically or haptically indicating no-fly zones or regions of the surgical site which the tool is not allowed to enter, and the like.

FIG. 1 is a plan view illustration of a Minimally-Invasive Robotic Surgical (MIRS) system 10, typically used for performing a minimally-invasive diagnostic or surgical procedure on a Patient 12 who is lying on an Operating table 14. The system can include a Surgeon's Console 16 for use by a Surgeon 18 during the procedure. One or more Assistants 20 may also participate in the procedure. The MIRS system 10 can further include a Patient-Side Cart 22 (surgical robot), and a Vision Cart 24. The Patient Side Cart 22 includes manipulators 23 which can manipulate at least one removably coupled instrument or tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by another manipulator 23 of the Patient-Side Cart 22 so as to position and orient the endoscope 28. The Vision Cart 24 can be used to process the images of the surgical site from the endoscope 28 for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 no longer being used at the time from the Patient-Side Cart 22, and replace it with another tool 26 from a tray 30 in the operating room. In exemplary embodiments, the robotic command module may be included (at least in part) in a processor of the Surgeons Console 16, while the tool correction module may be included (at least in part) in a processor of the Vision Cart 24, or in another associated processor structure.

Figure 2:
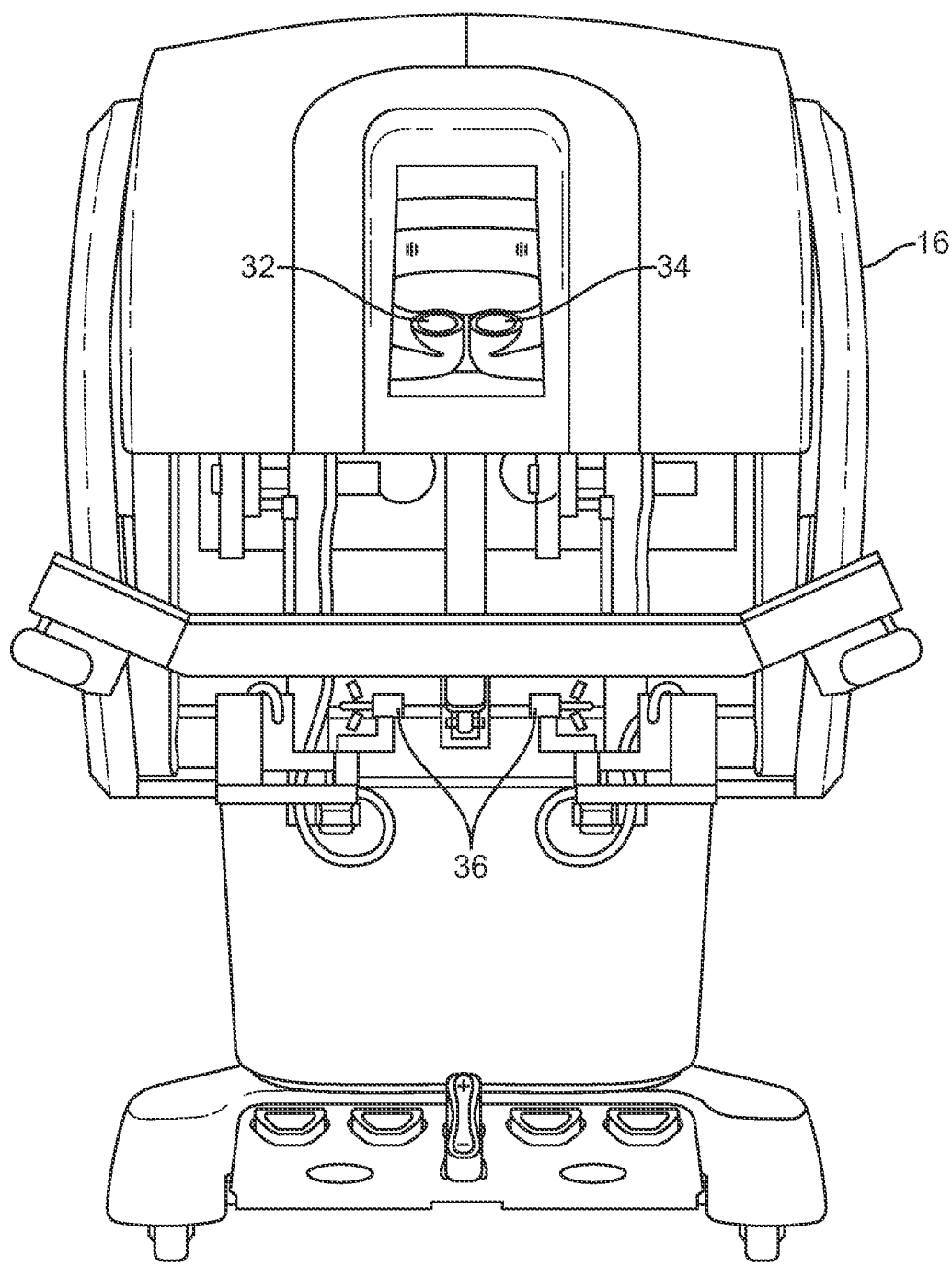
FIG. 2 is a front view of a surgeon's control console for a robotic surgery system.

FIG. 2 is a front side view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more control devices 36, which in turn cause the Patient-Side Cart 22 (shown in FIG. 1) to manipulate one or more tools. Preferably, control devices 36 will provide the same degrees of freedom as their associated tools 26 (shown in FIG. 1) so as to provide the Surgeon with telepresence, or the perception that the control devices 36 are integral with the tools 26 so that the Surgeon has a strong sense of directly controlling the tools 26. To this end, position, force, and tactile feedback sensors (not shown) are preferably employed to transmit position, force, and tactile sensations from the tools 26 back to the Surgeon's hands through the control devices 36.

The Surgeon's Console 16 is usually located in the same room as the patient so that the Surgeon may directly monitor the procedure, be physically present if necessary, and speak to an Assistant directly rather than over the telephone or other communication medium. However, it will be understood that the Surgeon can be located in a different room, a completely different building, or other remote location from the Patient allowing for remote surgical procedures.

Figure 3:
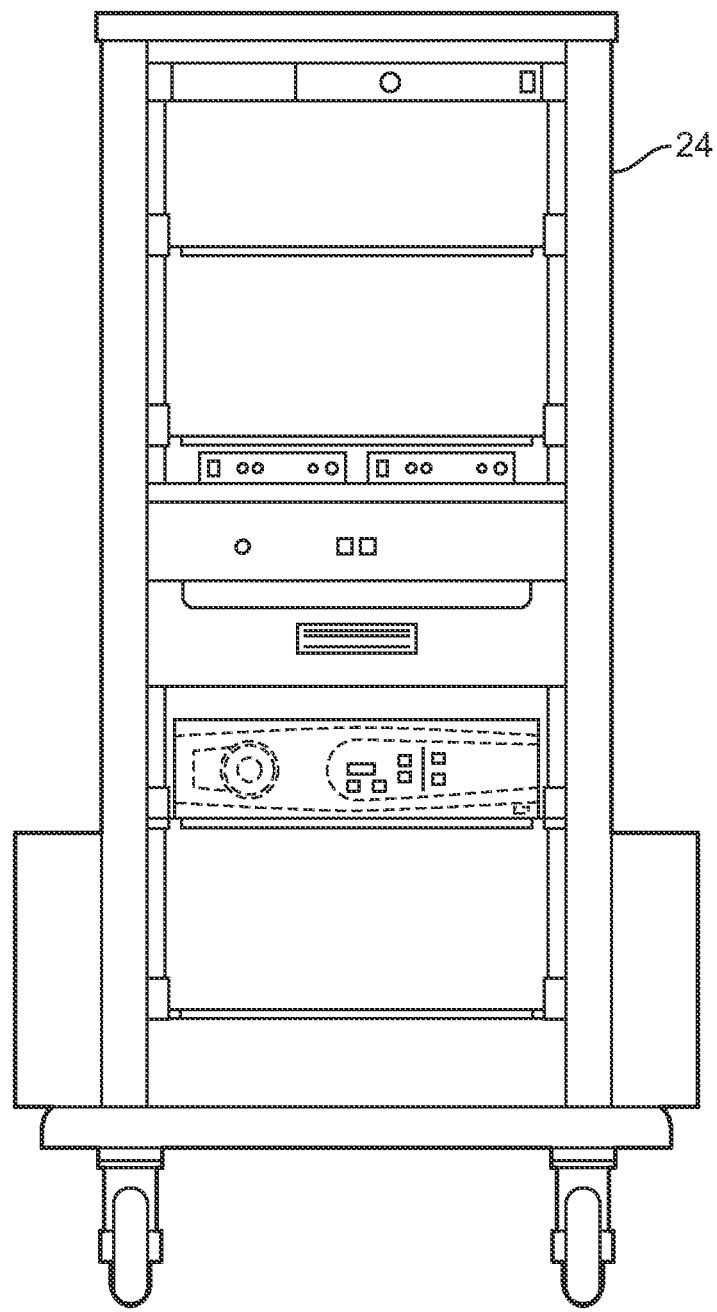
FIG. 3 is a front view of a robotic-surgery system vision cart.

FIG. 3 is a front-side view of a Vision Cart 24. Vision Cart 24 can be coupled with the endoscope 28 and can include a processor to process captured images for subsequent display, such as to a Surgeon on the Surgeon's Console, or on any other suitable display located locally and/or remotely. For example, where a stereoscopic endoscope is used, the Vision Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image-capture device, such as optical aberrations. Exemplary details of some of the possible image processing that can used are described in numerous patents and patent applications assigned to Intuitive Surgical, Inc. including, for example in U.S. Pat No. 7,277,120, the full disclosure of which is incorporated herein by reference.

Figure 4:
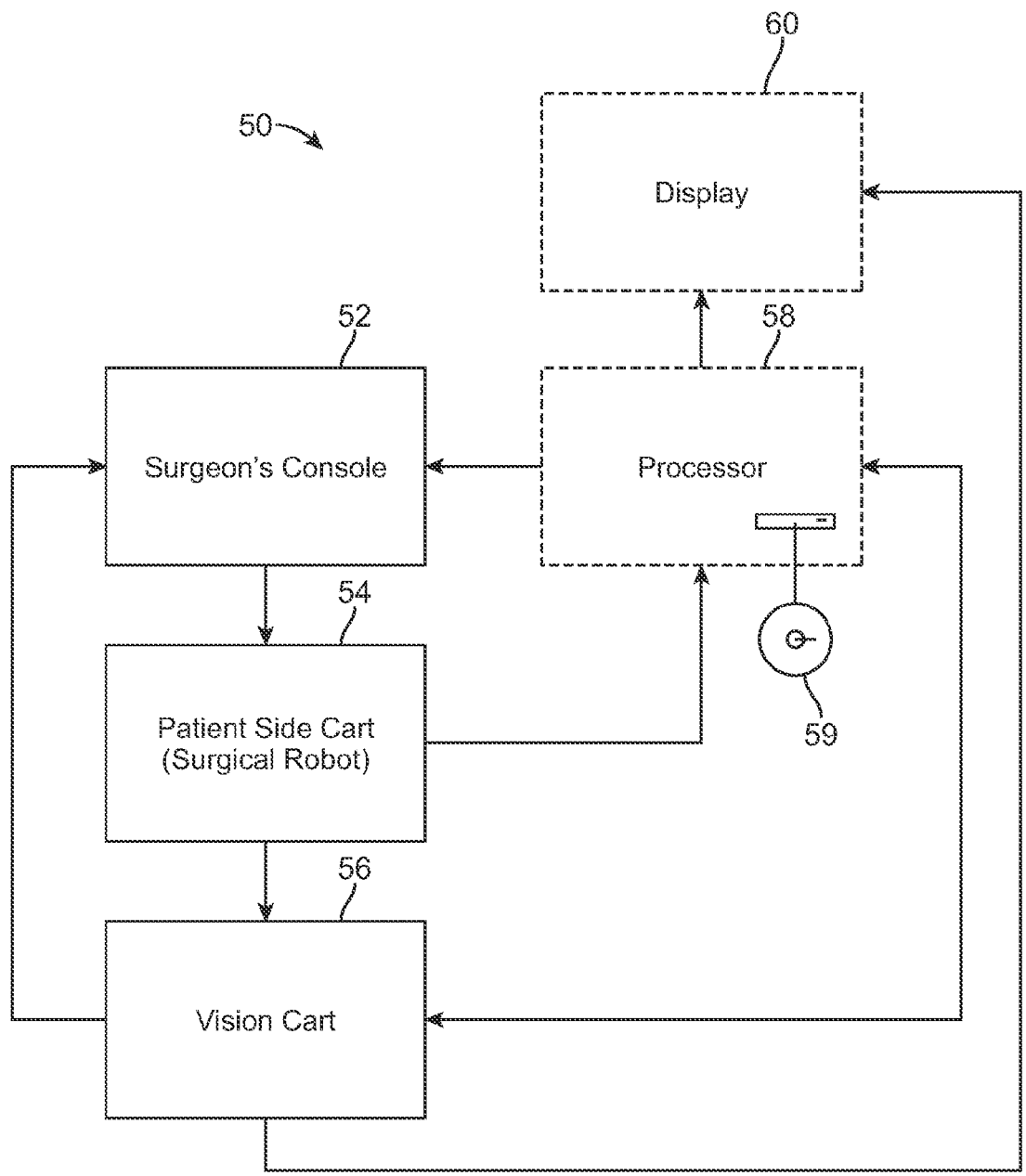
FIG. 4 diagrammatically illustrates a robotic surgery system.

FIG. 4 diagrammatically illustrates a simplified processing system of a robotic surgery system 50 (such as MIRS system 10 of FIG. 1), showing communication paths between major components or processors of the processor system. As discussed above, a processor of the Surgeon's Console 52 (such as Surgeon's Console 16 in FIG. 1) can be used by a Surgeon to control a Patient-Side Cart (Surgical Robot) 54 (such as Patent-Side Cart 22 in FIG. 1) during a minimally-invasive procedure, with the of the Surgeon's Console processor 52 typically including some or all of the functionality of a robotic command module. Hence, the Surgeon's Console processor 52 calculates movement command signals using joint data from the patient-side Cart 54. The Patient-Side Cart 54 can use an imaging device, such as a stereoscopic endoscope, to capture images of the procedure site and output the captured images to a Vision Cart 56 (such as Vision Cart 24 in FIG. 1). A processor of Vision Cart 56 can process the captured images in a variety of ways prior to any subsequent display. Alternatively, the Patient-Side Cart 54 can output the captured images for processing outside the Vision Cart 56. For example, the Patient-Side Cart 54 can output the captured images to a processor 58, which can be used to process the captured images. Hence, the functionality of the image correction module may optionally be implemented at least in part in the Vision Cart processor 56 or in processor 58. The images can also be processed by a combination the Vision Cart 56 and the processor 58, which can be coupled together so as to process the captured images jointly, sequentially, and/or combinations thereof. One or more separate displays 60 can also be coupled with the processor 58 and/or the Vision Cart 56 for local and/or remote display of images, such as images of the procedure site, or any other related images.

Each of the processors described herein will typically include one or more processing boards or circuits and one or more tangible medium 59 embodying computer-readable instructions or software for implementing some or all of the method steps described herein. Tangible medium 59 may comprise an optical recording media such as a compact disk or digital video disk, a magnetic recording media such as a hard disk drive, a floppy disk, a backup tape, or the like; a memory such as a read-only memory, a random access memory, a non-volatile memory, a memory stick, or the like.

The software or code defined by tangible medium 59 may be transmitted to the processor via the tangible recording medium, an internet or other network system, a wireless signal transmission, or the like. While schematically shown in FIG. 4 as the tangible medium associated with processor 58, the software may reside in a number of different processors including processors of the surgeon's console 52, a patient side cart 54, vision cart 56, and/or processor 58. Hence, the software may run on one or more processor circuits or processor boards that are physically mounted to one or more of the components of the robotic surgery system 50 in any of a wide variety of centralized or distributed data processing system architectures. Similarly, the software may be written as a single monolithic code, but will often be broken down into a series of subroutines, with differing portions of the code optionally running on differing processor boards. The functionality attributed to modules described herein will often be implemented as software (including software code embodied on tangible medium 59), hardware (including a processor circuit of processor 58 or one of the other processor boards of robotic surgical system 50), and/or a combination of software and hardware suitable for the ascribed data processing tasks.

Robotic-Surgery Tool Tracking

Figure 5C:
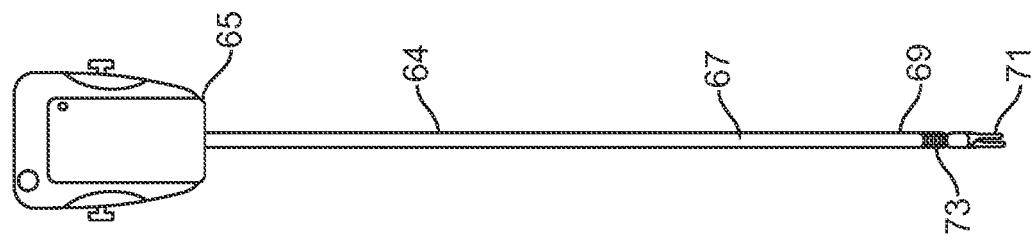
FIGS. 5B and 5C are respective front views of an 8 mm shaft robotic surgery tool and a 5 mm shaft robotic surgery tool.
Figure 5B:
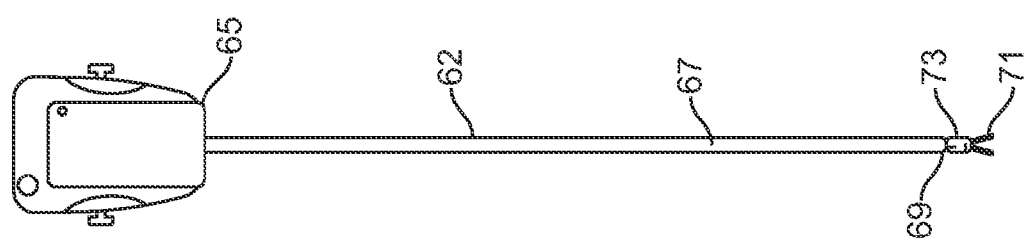
Figure 5A:
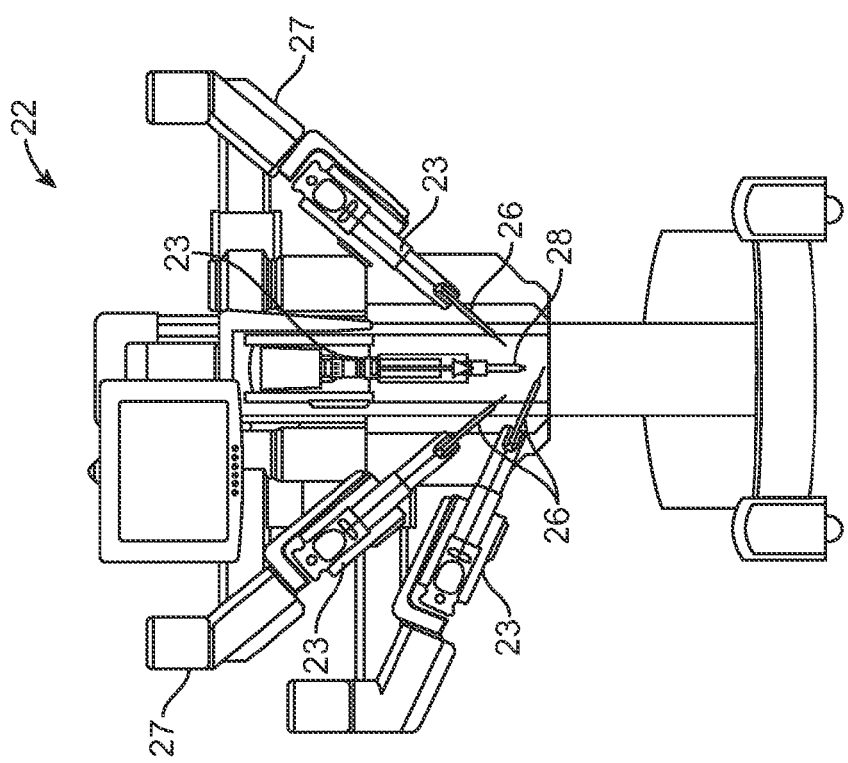
FIG. 5A is a front view of a patient-side cart (surgical robot) of a robotic-surgery system.

FIGS. 5A, 5B, and 5C show a Patient-Side Cart 22, an 8 mm shaft surgical tool 62, and a 5 mm shaft surgical tool 64, respectively. Surgical tools 62 and 64 are examples of surgical tools 26. The Patient-Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 (e.g. the end effectors 66) can be positioned and manipulated through incisions in the patient so that a kinematic pivotal center 25 (see FIG. 1) is maintained at the incision so as to minimize the size of the incision. Images of the surgical site can include images of distal ends of the surgical tools 26 when they are positioned within the field-of-view of the imaging device 28.

As can be understood with reference to FIGS. 1 and 5A, each tool 26 is typically supported by a manipulator 23. The manipulator moves during surgery under the direction of a processor of surgeon's console 16 so as to move an end effector of the tool within the internal surgical site per an input movement command. Manipulators 23 are generally supported by a passive support linkage 27 so as to allow the manipulators and tools to be positioned manually in preparation for surgery. The support linkages 27, sometimes referred to as set-up joints, also allow the position and orientation of tools to be changed during a procedure, with an assistant 20 typically withdrawing the tool, releasing the set-up joints from a fixed configuration to a manually movable configuration, moving the manipulator 23 to a new and desired location, and again fixing the set-up joints. Joint-based data is provided from both the manipulator 23 and the support linkage 27 to the processor of the surgeon cart 16 for calculation of movement commands in response to the input from the surgeon 18.

Referring now to FIGS. 5B and 5C, tools 62, 64 typically include a proximal end 65 supportable by a manipulator 23, and an elongate shaft 67 that extends from the proximal end to a distal end 69. An end effector 71 is coupled to distal end 69 of shaft 67 by a linkage 73, with the end effector and linkage generally being driven by motors of linkage 23. In alternative embodiments, at least some of the degrees of freedom of the set-up joints may be powered, and/or some of the degrees of freedom of the manipulator may be passive. The pivotal center may be defined by a parallel linkage structure of manipulator 23 (encompassed within the term remote center linkage), or a passive joint of the manipulator may allow for natural or environmentally imposed pivoting of the tool about the aperture into the patient. Still further alternatives are possible, including redundant joint driven linkages which allow a calculated remote center of pivotal movement to be provided.

Figure 6:
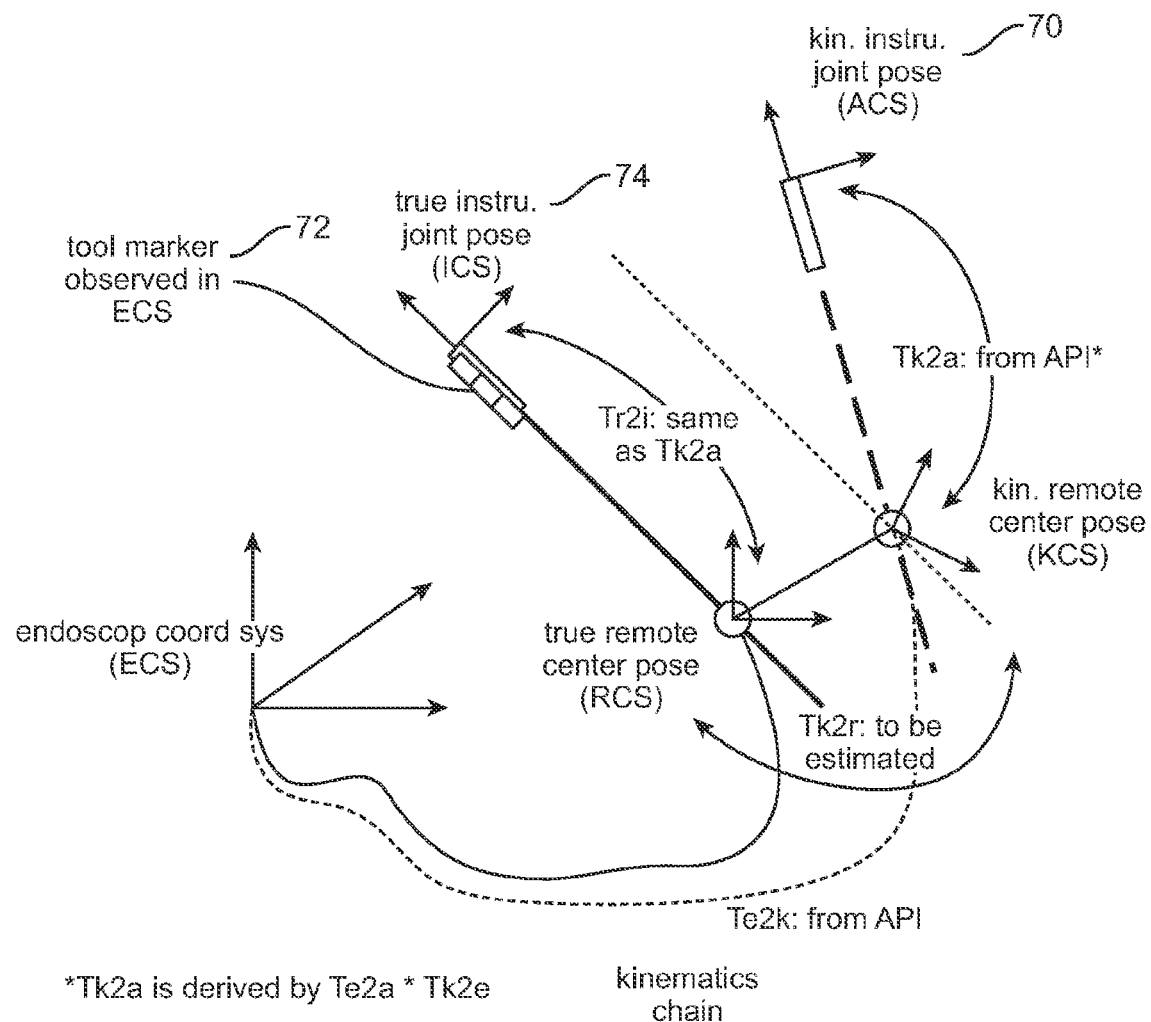
FIG. 6 diagrammatically illustrates relative differences between a kinematics-estimated tool pose, a image-derived estimated tool pose, and a true tool pose.

FIG. 6 diagrammatically illustrates relative differences between a kinematics-estimated surgical tool pose 70, an image-derived estimated surgical-tool pose 72, and a true surgical-tool pose 74. As discussed above, accurate information of a tool's 3d pose is important for a number of image-guided surgical and user-interface applications. When kinematic-joint sensor data is used to estimate the tool's 3d pose, a significant amount of error can be introduced. Although many sources of error exist, such as random sensor noise, a predominant portion of this error can be attributed to offset error, which arises due to fixed differences between a kinematic joint's true position and a kinematic joint's indicated position as indicated by kinematic-joint sensor data. Offset errors in kinematic joints located further away from the tools's distal working end typically contribute more to the total offset error than joints located closer to the tool's distal working end. As a result, a kinematics-estimated pose 70 can deviate significantly from a true pose 74 for the surgical tool. For example, a kinematics-estimated tool pose for an exemplary surgical robot may differ from a true pose for the tool by up to 10 to 15 mm on a well calibrated system, and even more if the system has not been recently and/or accurately calibrated. As a result, it can be advantageous to use non-kinematics based methods to obtain more accurate tool pose estimates, which can be used to determine a positional correction for use in correcting the kinematics estimates.

An image-derived tool pose estimate 72 can be significantly more accurate than a raw-kinematics estimated tool pose 70. This increased accuracy is diagrammatically illustrated in FIG. 6 by the relatively small positional difference between the image-derived tool pose 72 and the true tool pose 74 shown. However, an image-derived tool pose 72 may be available at a significantly lower rate than a raw-kinematics estimated tool pose due to a number of factors, such as image processing times, and at certain times may not be available at all where the tool is outside the view of the imaging device, or is occluded for some reason (such as by patient tissue, by patient bodily fluids, and/or by opaque or translucent vapors due to cauterization or the like).

Figure 7:
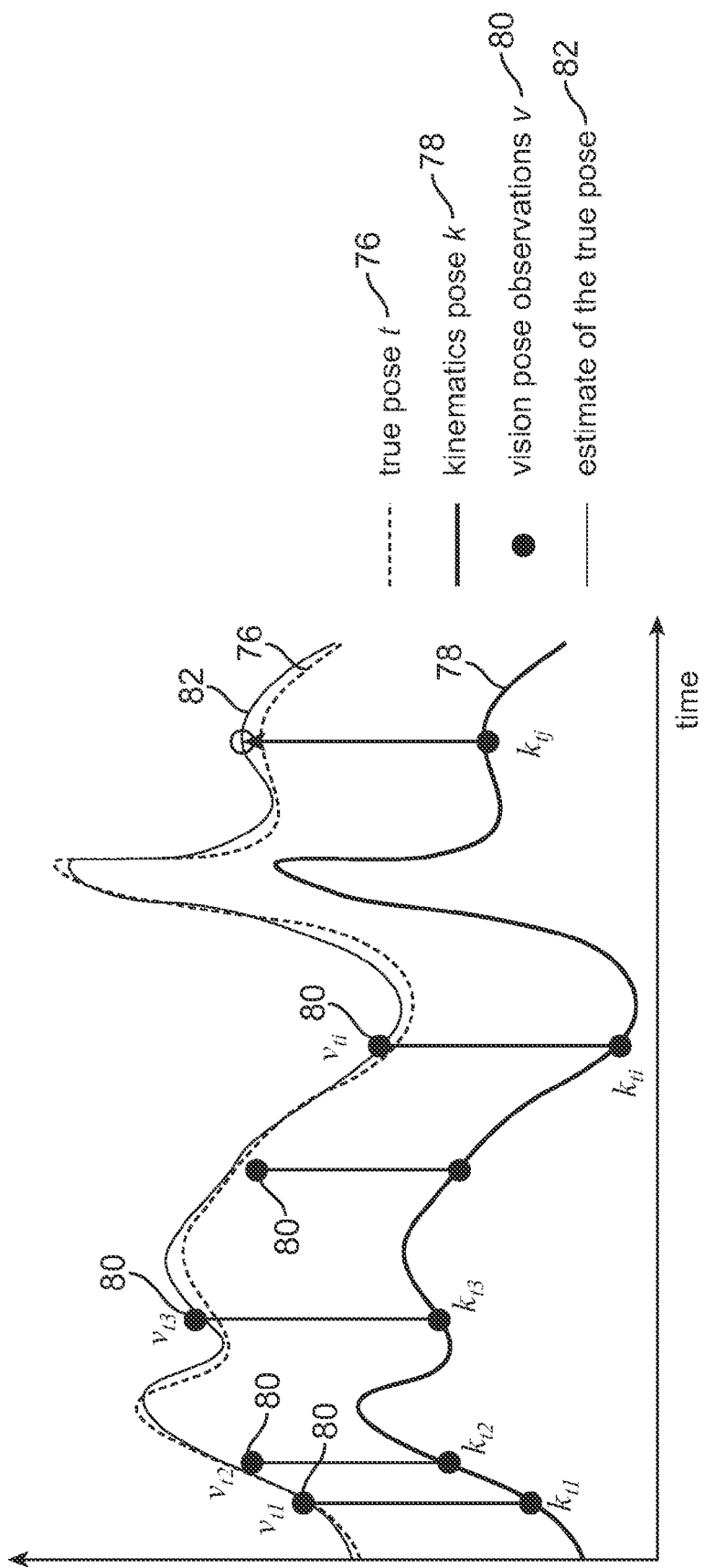
FIG. 7 diagrammatically illustrates variations with time of a raw-kinematics estimated tool pose, a image-derived estimated tool pose, an estimate of the true tool pose, and a true tool pose.

FIG. 7 diagrammatically illustrates variations with time between various estimated poses and the true pose 76 of a tool. As shown, a raw-kinematics estimate 78 for a pose for the tool can deviate significantly from the true pose 76. As discussed above, a predominant portion of this deviation may be associated with a fixed offset error, which is illustrated by way of the substantially constant offset between the raw-kinematics estimate 78 and the true pose 76. Due to the relatively high rate of availability of kinematics sensor data, the raw-kinematics estimated pose 78 can be available at a high rate, such as 1333 times per second. In contrast, an image-derived pose estimate 80 may be available at a lower rate, but can be relatively more accurate. Advantageously, a combination of kinematics-estimated poses and image-derived estimated poses can be used to determine a true pose estimate 82, which may track the true pose 76 relatively well. Details of exemplary techniques for fusion or combination of raw-kinematics estimated poses and image-derived estimated poses for the determination of a true pose estimate 82 are described in patents and patent applications assigned to Intuitive Surgical, Inc. including, for example in U.S. Pat. Pub. No.

2006/0258938 A1, the full disclosures of which is included herein by reference. Many of these techniques can be improved and/or made more efficient by the structures and methods described herein.

Referring now to FIGS. 6 and 7, errors in the joint or kinematic-based end effector pose may come from a variety of sources. More specifically, the kinematic data errors may arise primarily from errors in zero calibration of the potentiometers or other joint sensors along the kinematic chains of the endoscope and/or tool, structural inaccuracies (including tolerance errors in the link lengths of the linkages on the kinematic chain, deformation of the links of the kinematic chain, and the like) for the kinematic chains supporting the endoscope and/or tool, or a combination of both. Errors from the set-up joints may have more influence because they are more proximal to the kinematic chain base, and they have longer links. These set-up joint errors will largely result in the pose error of the pivotal center, which generally does not move significantly during tissue manipulation with the associated tool.

Work in connection with the present invention has indicated that instrument location error may primarily be due to pose error of the pivotal center. This may allow a significant simplification for fusion of kinematic and image-based data. To facilitate descriptions of the preferred approach, the terms coordinate system and pose may both reference a rotation (or orientation) and translational position. Hence, these terms may be used interchangeably as a pose also defines the coordinate system. An endoscope camera manipulator or ECM may define a camera tip coordinate system effectively attached to the distal tip of the endoscope. The origin may be disposed at the center of the stereoscopic camera, with the Z axis oriented toward the image seen. When the ECM is moved, the kinematic information may be automatically updated. Each individual camera may have an associated camera coordinate system, with the cameras of a stereoscopic endoscope typically being angularly offset and oriented toward the surgical scene so as to provide depth or Z axis information.

As the exemplary robotic surgical system employs a remote-center manipulator linkage assembly, the pivotal center of the tool may generally be referenced herein as a remote center. The actual remote center has an associated true remote center coordinate system RCS having an origin at the pivotal center of the tool shaft. This true remote center coordinate system may be offset from a kinematics remote center coordinate system KCS which is derived from joint-based data, but which reflects the errors in that data in the kinematic calculations associated therewith. There may also be one coordinate system attached to each rigid segment of the robotic linkage, with that coordinate system being referenced as a true instrument joint coordinate system ICSi, where i denotes the i-th active joint as counted distally from the setup joints. A kinematic instrument joint coordinate system ACSi may be derived for each link or segment using joint-based kinematic data.

Figure 17:
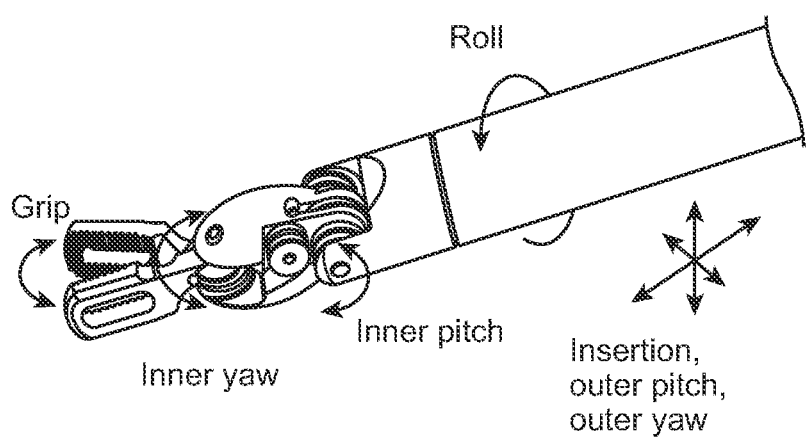
FIG. 17 graphically illustrates degrees of freedom of an exemplary robotic surgical instrument.

The tool manipulator may pivot the shaft during the movements of the end effector about two axes that intersect at the pivotal center, with the two axes being referred to as an outer pitch axis and an outer yaw axis. As shown in FIG. 17, the manipulator may also move the tool axially through the minimally invasive aperture along the insertion axis. The tool may provide a roll axis, an inner pitch axis, an inner yaw axis, and a grip actuation. Similarly, the image capture device may include an elongate shaft which is pivoted by the camera manipulator at a camera pivotal center about a camera pitch axis and a camera yaw axis, as well as having an insertion axis along the camera shaft.

Due to the configuration of active joints in the exemplary manipulator, the fixed translational error or positional offset of the remote center pose will result in varying translational error of the instrument shaft pose when the rotational offset is non-zero. Rotational offset is generally effectively invariant during tissue manipulation with a tool. The pose offset or bias of the remote center is estimated below. Such remote center pose offset estimations and calculations differ from estimating an offset of the instrument shaft alone, as the remote center location remains at the pivotal center when the shaft moves axially.

The remote center offset is able to absorb the offset of two active joints of the manipulator: outer pitch and outer yaw (inner pitch and inner yaw being distal of the remote center and associated with movement of the end effector relative to the shaft). In other words, if remote center pose error and outer pitch/yaw bias are the only error in the system, the estimated remote center pose offset is able to compensate for all the error and result in an error free system no matter how the active joints move. However, as the estimated remote center pose can have other errors, those other errors may be absorbed and reflected in the outcome of the estimate. Offset of the shaft roll or rotation of the instrument about the shaft's axial center may not be reflected in the remote center offset.

Figure 8:
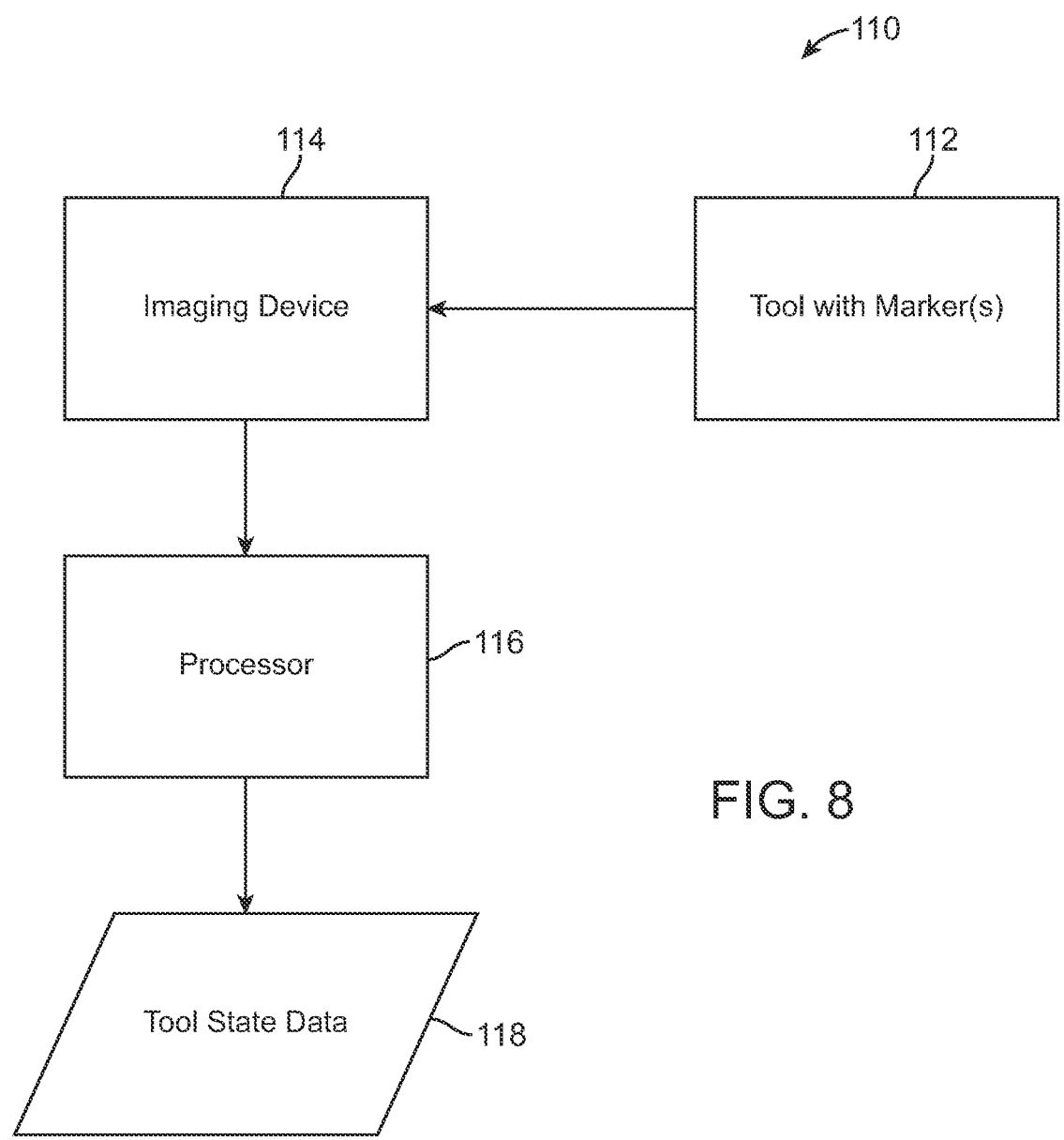
FIG. 8 diagrammatically illustrates a system for tracking tools with markers.

FIG. 8 diagrammatically illustrates a system 110 for tracking a tool with marker(s) 112. The system includes at least one tool with a marker(s) 112, similar to the tool 26. An imaging device 114, such as the stereoscopic endoscope 28, is used to capture one or more image(s) of the tool with marker(s) 112. The imaging device 114 is coupled with a processor 116 and transfers image data to the processor 116 in response to imaging the tool with marker(s) 112. The processor 116 is configured to process the received image data so as to generate tool state data 118, which can include an estimated 3d pose for the tool with marker(s) 112.

Figure 9:
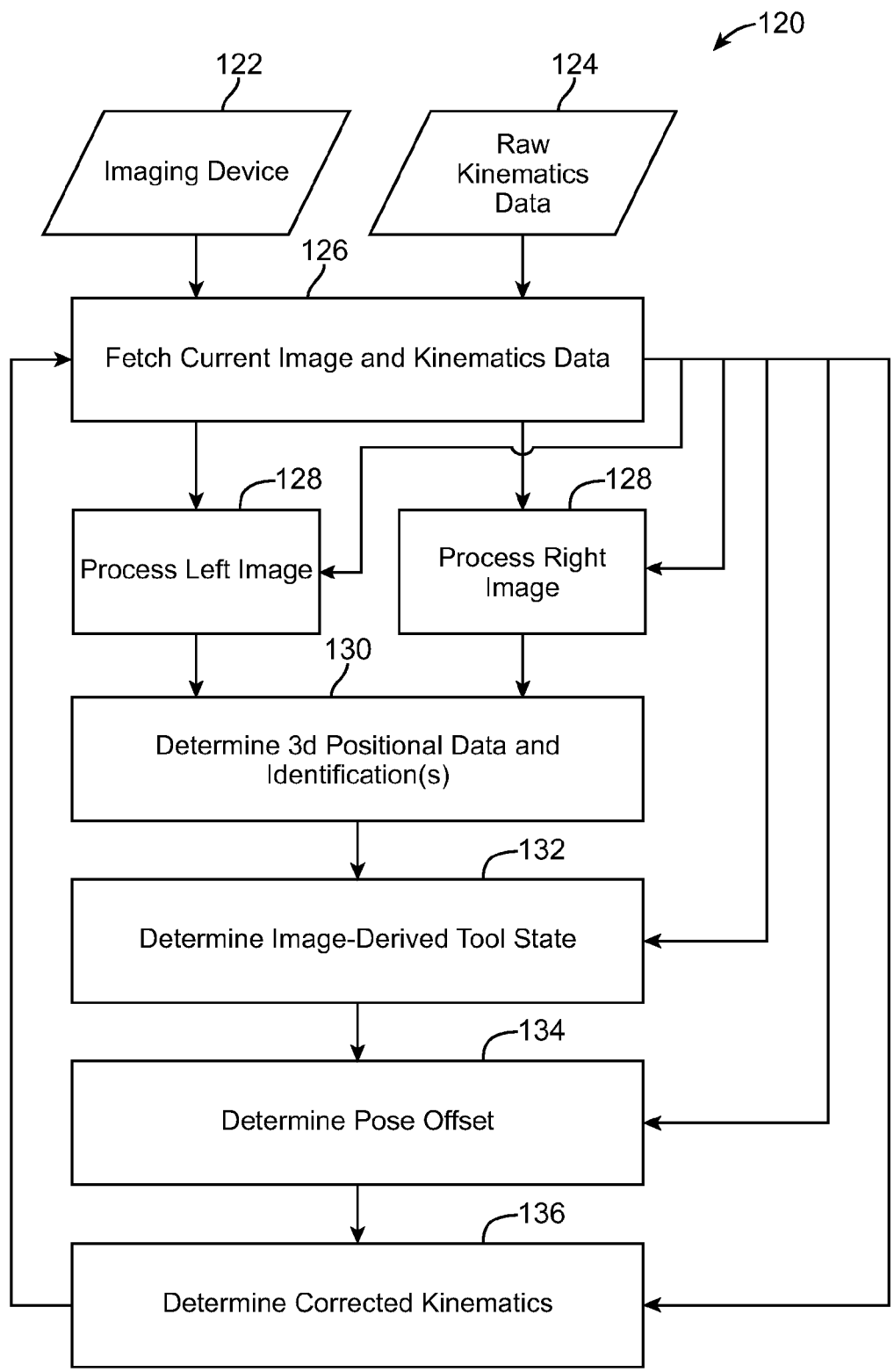
FIG. 9 is a flow diagram of a tool tracking method for determining a tool state showing steps for processing stereoscopic images of markers and kinematics data to generate a corrected-kinematics estimated tool state using an image-derived pose offset.

FIG. 9 is a flow diagram of a tool tracking method 120 for determining a tool state showing steps for processing stereo images of markers and raw-kinematics data to generate a corrected-kinematics estimated tool state using an image-derived 3d pose offset. Because of the higher-update rate of the joint sensor data used to generate an estimated tool state from raw-kinematics data 124 as compared to an image-derived estimated tool state, an image-derived pose offset can be combined with an estimated tool state from raw-kinematics to generate a corrected-kinematics estimated tool state. In this way, a series of corrected-kinematics estimated tool states can be generated using a single pose offset combined with a corresponding series of estimated tool states from raw-kinematics data 124. The pose offset can be updated over time in response to new image data 122.

The determination of a pose offset starts in step 126 with the acquisition of image data of the tool with marker(s) and corresponding raw kinematics data 124 for the tool with marker(s). As shown, the image data 122 can include left image data and right image data, but it should be understood that a single image of one or more marker features can be processed so as to generate image-derived positional information useful in generating a pose offset. For example, the location within an image of a single marker feature can provide two mathematical constraints towards a solution. Where a single image contains four non-collinear features, the locations of the four non-collinear features within the image are sufficient to determine an image-derived 3d pose for the tool. Where stereo images contain three non-collinear features, the locations of the three non-collinear features within the stereo images are sufficient to determine an image-derived 3d pose for the tool. The raw-kinematics data 124 can include basic sensor data, such as kinematic joint position parameters, and/or can include a current raw-kinematics derived tool state. Advantageously, all the constraints or information desired for a unique solution do not need to be acquired in a single image frame. For example, the solution can be computed using constraints identified from multiple images frames, each one of which alone is insufficient to uniquely determine the solution.

Figure 16:
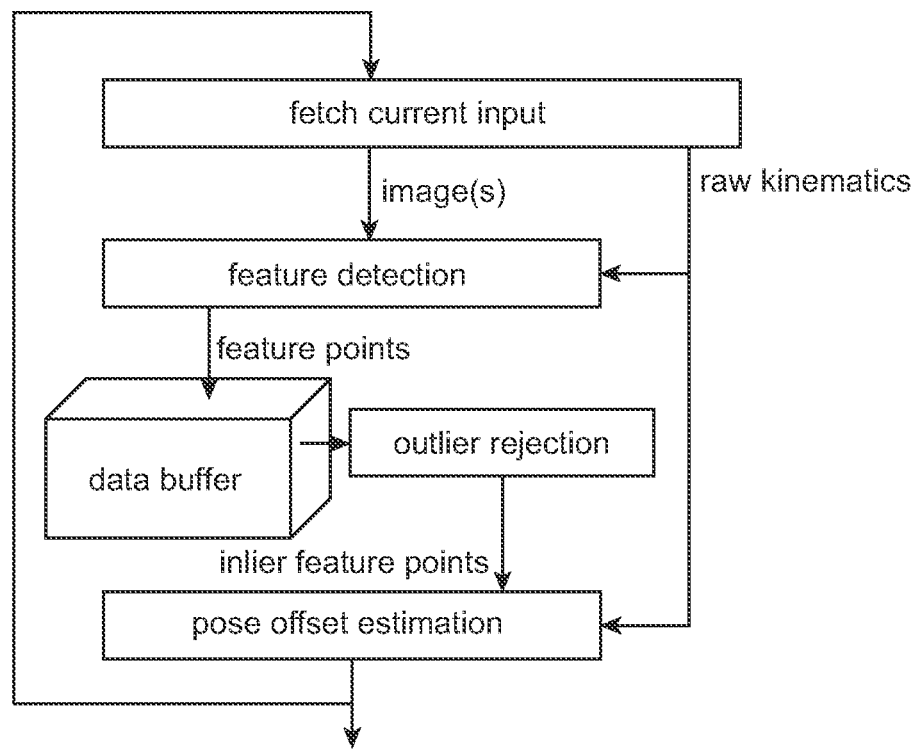
FIG. 16 is a flow chart of a method for rejecting outlier image data so as to more robustly fuse image-based data with joint-based kinematic data.

In step 128, the left image and the right image are processed so as to detect marker features. The position of the marker(s) feature(s) within the left image and the position of the marker(s) feature(s) within the right image are used in step 130 to generate three-dimensional coordinates for the marker(s) feature(s). Note that not all marker features that initially appear to be detected have to be (or even should be) used for all subsequent pose calculations. It is possible, for example, that the feature extraction routines can have false positives due to coincidental alignment of combinations of foreground and background image features that have configurations similar to those of a marker. This can occur more often with markers that are relatively simple, so that the marker does not have much redundancy. Such false positive marker detections will typically represent outlier pose data, and will preferably be identified and eliminated so as to provide a more robust and accurate estimation of the image-based tool pose. Otherwise, incorporating of these outliers in the estimation process can cause the result to degrade significantly. Identifying a false positive marker detection from a single image frame taken at one time (or even from concurrent left and right image frames) may be challenging. However, the detection of actual markers in sequential image frames should exhibit appropriate consistency in their associated estimation of kinematic bias or pose offset, particularly when the bias between the image-based pose estimation and the joint-based pose estimation is assumed to be static. When the stationary kinematic bias remains unknown and to be estimated, simultaneous estimation of the bias and outlier rejection can be done through a variety of robust estimation techniques. Random Sample Consensus (RANSAC) outlier rejection techniques may be particularly beneficial for avoiding pose errors, and additional aspects of these techniques were described by Martin A. Fischler and Robert C. Bolles in "Random Sample Consensus: A Paradigm for Model Fitting with Applications to Image Analysis and Automated Cartography". Comm. Of the ACM 24: 381-395 (June 1981). Applying this RANSAC outlier rejection method on a sliding window can be sufficient for outlier rejection, and an exemplary outlier rejection technique is schematically illustrated in FIG. 16. More generally, a combination of a relatively low discriminative marker configuration and temporal constraints on marker positioning facilitates use of simpler markers having less visual content (and hence markers providing less information) to achieve useful detection confidence.

A number of refinements can be implemented to make the processing of the images more efficient. For example, when an instrument is being tracked and the instrument location has been determined in one or more images, the instrument location in a subsequent image can be predicted using the kinematic data from step 126, optionally together with trajectory history and/or kinematic trajectory information for that instrument. The location information from prior images can be used to derive an instrument region of interest (ROI) in the images so that only smaller portions of the images are processed so as to identify the new instrument location. This can both reduce the computational requirement and avoid the distraction of other features from background far away from the instrument.

In step 132, the three-dimensional coordinates for the marker(s) features(s) can be processed in combination with any identification(s) of markers(s) so as to determine an image-derived tool state. Although images of a number of markers can be used to provide sufficient pose information for determining a 3d pose for the tool, it can be advantageous for a single marker to contain a sufficient number of features for determining a 3d pose for the tool. Additionally, it can be advantageous for each marker on a tool to have an identification that differs from neighboring markers. With such a marker, an image-derived tool state can be determined by determining the 3d pose of the marker, determining the identification of the marker, and using data regarding how the identified marker is positioned and oriented on the tool. It is appreciated that variations of this approach can be used. For example, features from a combination of markers can be combined to determine the 3d pose of the combination of markers, which can be combined with data regarding how the features from the combination of markers are positioned and oriented on the tool. During this process, a corrected-kinematics estimated tool state (from a previously determined pose offset) can be compared against the image-derived estimated tool state so as to reject any image-derived estimated tool states that differ too much from the corrected-kinematics estimated tool state.

In step 134, the pose offset is determined so that it can be combined with a raw-kinematics data 124 estimated tool state to obtain a corrected-kinematics estimated tool state. It is appreciated that a variety of approaches may be used to determine the pose offset. For example, the pose offset can be calculated as a difference between an estimate of the true tool pose (shown in FIG. 7) and a corresponding raw-kinematics data 124 estimated tool state for substantially the same point in time. As a further example, the pose offset can be calculated as a difference between an image-derived estimated tool state and a corresponding raw-kinematics data 124 estimated tool state for substantially the same point in time.

In step 136, a corrected-kinematics based tool state is determined. As discussed above, a single pose offset can be used to correct one or more raw-kinematics data 124 based tool states so as to compensate when raw-kinematics data 124 based tool states are available at a higher rate as compared to image-derived tool states. The corrected kinematics can then be provided back to the start of the process (step 126), where the "fetched" current image and kinematics data can include image data, raw kinematics data, and the current pose offset and/or corrected-kinematics data.

Figure 10:
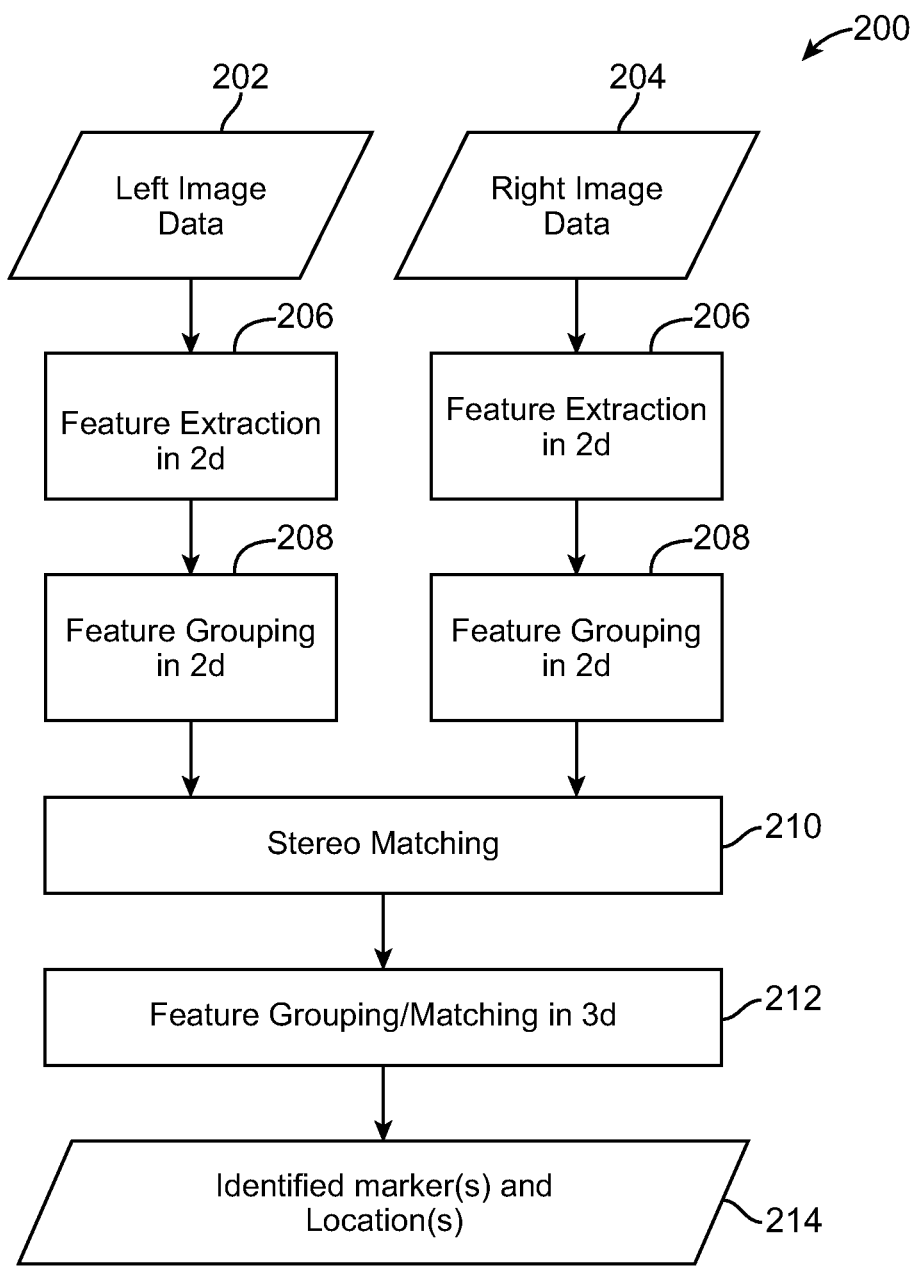
FIG. 10 is a flow diagram of a method for processing stereoscopic images of tool-tracking markers.

FIG. 10 is a flow diagram of a method 200 for processing stereoscopic endoscope images of tool-tracking markers. In step 206, left image data 202 and right image data 204 are processed to extract primitive image features. "Primitive image features" refers to visually salient features that can be detected locally, such as blobs and corners. A blob is a small patch with sufficient contrast with respect to its surroundings. A corner is the intersection of two edges. A Maximum Stable Extremal Region (MSER) approach provides an excellent way to detect blobs at an affordable cost.

There are many ways to detect corner points from images. For more specific corners (e.g. a saddle point), analysis can be done on the result of the above generic corner detectors to look for the desired properties. A learning-based approach is also available for dot detection that considers the fine appearance of the dot to disambiguate with background dots.

The output from a blob detector is a list of blobs from the image. It can be much faster to analyze these blobs than all the image pixels. We detected the bars of the two-dimensional markers by checking their flatness (the ratio of the first and second eigen values of the covariance matrix). We detected circles by a simple heuristics that the centroid of a bright blob is inside the bounding box of a dark blob and the bounding box of the dark blob is fully contained by the bounding box of the bright blob.

Following the extraction of the primitive image features, the remaining steps of method 200 can be accomplished. In step 208, the extracted features are grouped. Grouping refers to the process of establishing correspondences between the extracted primitive features and the object being imaged, such as a particular marker. Grouping can either occur in two dimensions (typically in image space) or in three-dimensional space. This process also accounts for extracted features that belong to the background instead of the object. The primitive feature grouping relies on knowledge of the marker's configuration to assemble extracted features into groups of features belonging to any particular marker. In step 210, the grouped features of the left image data 202 are matched with corresponding grouped features of the right image data 204. In step 212, the stereo-image matched features can be processed to determine three-dimensional data for the features. The three-dimensional data for the features can be processed so as to identify the marker and determine a three-dimensional pose for the marker (data 214), which can then be used to determine a three-dimensional pose for the tool having the marker. More details on an exemplary tool marker system and image tracking technology may be seen in U.S. patent application Ser. No. 12/428,657 filed on Apr. 23, 2009, entitled "Fiducial Marker Design And Detection For Locating Surgical Instruments In Images", the full disclosure of which is incorporated herein by reference.

The methods shown schematically in FIGS. 9 and 10 make use of both left and right image data from a stereoscopic imaging system. Simplified approaches may be employed in a monocular system by following only one of the two parallel left/right image processing paths. Monocular fusion systems may, like stereoscopic fusion systems, provide significant benefits in pose accuracy, particularly when a time series of images are available showing a tool at differing poses. Similarly, these and the other methods described above can be implemented using a variety of calculation approaches. Exemplary tools for performing some of these calculations are provided below. We use superscript for the coordinate system where the entity is defined, and subscripts for different things as explained or understood in context. Reference is again made to FIG. 6 for the coordinate system descriptions which follow.

We denote the endoscope coordinate system ECS=$\{c_E, x_E, y_E, z_E\}$ where $c_E$ is the origin of the coordinate system and $\{x_E, x_E, x_E\}$ are the axes. Since our discussions are with respect to the ECS, we choose to set $c_E=[0,0,0]^T$, $x_E=[1,0,0]^T$, $y_E=[0,1,0]^T$, $z_E=[0,0,1]^T$.

The true remote center coordinate system RCS=$\{c_R^E, x_R^E, y_R^E, z_R^E\}$, where $c_R^E$ is the coordinate of the origin of RCS in ECS, $\{x_R^E, y_R^E, z_R^E\}$ are the coordinate of the axis vectors of RCS in ECS.

The joint-based (or kinetic) remote coordinate system KCS=$\{c_K^E, x_K^E, y_K^E, z_K^E\}$, following same convention as RCS. It is derived from forward kinematics.

Similarly, the true instrument coordinate system ICS=$\{c_I^E, x_I^E, u_I^E, z_I^E\}$, and kinetic or joint-based instrument coordinate system ACS=$\{c_A^E, x_A^E, y_A^E, z_A^E\}$. Note the other coordinate systems are all defined in ECS.

p is a point in 3d. Its coordinates in RCS is $p^R=[p_x^R, p_y^R, p_z^R]^T$ and its coordinate in ECS is $p^E=[p_x^E, p_y^E, p_z^E]^T$. Their relationship is:

$$p^E = R_R^E \cdot p^R + c_R^E. \tag{1}$$

where rotation matrix $$R_R^E = \begin{bmatrix} | & | & | \\ x_R^E & y_R^E & z_R^E \\ | & | & | \end{bmatrix} = \begin{bmatrix} - & (x_E^R)^T & - \\ - & (y_E^R)^T & - \\ - & (z_E^R)^T & - \end{bmatrix}$$

The inverse transformation is $$p^R = R_E^R \cdot p^E - R_E^R c_R^E \tag{2}$$

where $-R_E^R \cdot c_R^E = c_E^R$. This is also a general equation for any coordinate transformation between two CS or coordinate systems.

R and t can be combined in a single 4 by 4 matrix T in the homogeneous coordinate system.

$$T_R^E = \lfloor R_R^E | c_R^E \rfloor \tag{3}$$

$$T_E^R = (T_R^E)^{-1} = \lfloor (R_R^E)^T | -(R_R^E)^T c_R^E \rfloor \tag{4}$$

The exemplary movement command processor reports the following relevant information for each patient side manipulator tool or PSM:

Remote center pose $\{R_K^E, c_K^E\}$. It defines the following equations:

$$p^E = R_K^E p^K + c_K^E \tag{5}$$

$$p^K = (R_K^E)^{-1} p^E - (R_K^E)^{-1} c_K^E \tag{6}$$

Active joint angles $\Theta_a = \lfloor \theta_{a0}, \ldots, \theta_{ag} \rfloor$: With remote center as base and apply forward kinematics using the $\Theta_a$ we will get $\{R_{Ai}^E c_{Ai}^E\}$ for each segment of the PSM.

$$p^E = R_A^E p^A + c_A^E \tag{7}$$

$$p^A = (R_A^E)^{-1} p^E - (R_A^E)^{-1} c_A^E \tag{8}$$

By eliminating $p^E$ using Eqn. 5 and Eqn. 7, we have $$p^K = (R_K^E)^{-1} R_A^E p^A + (R_K^E)^{-1} (c_A^E - c_K^E) \tag{9}$$

Therefore $$R_A^K (R_K^E)^{-1} R_A^E \tag{10}$$

$$c_A^K = (R_K^E)^{-1} (c_A^E - c_K^E) \tag{11}$$

And $$p^A = (R_A^E)^{-1} R_K^E p^K + (R_A^E)^{-1} (c_K^E - c_A^E) \tag{12}$$

therefore $$R_K^A = (R_A^E)^{-1} R_K^E \tag{13}$$

$$c_K^A = (R_A^E)^{-1} (c_K^E - c_A^E) \tag{14}$$

We may assume that the joint angles are accurate for the PSM active joints. Therefore $T_I^R = T_A^K$.

$$p^R = (R_K^E)^{-1} R_A^E p^I + (R_K^E)^{-1} (c_A^E - c_K^E) \tag{15}$$

$$p^I = (R_A^E)^{-1} R_K^E p^R + (R_A^E)^{-1} (c_K^E - c_A^E) \tag{16}$$

Remote Center Correction $R_R^K, c_R^K$ are the remote center pose corrections to solve for.

$$p^K = R_R^K p^R + c_R^K \tag{17}$$

$$p^R = (R_R^K)^{-1} p^K - (R_R^K)^{-1} c_R^K \tag{18}$$

Image Observation Generation of Model Markers

Joint-based or kinematic information from the robotic command calculation module may be designated auxiliary processor information or API. We want to derive the equations for how a marker point defined in ACS ($p^A$) can be observed in ECS ($p^E$) expressed by known transformations from API and unknown transformation between KCS and RCS. This summarizes the data generation process. The steps to follow may include: $p^E \to p^K \to p^R \to p^I$. This can be done by iteratively by plugging in Eqn. 6, Eqn. 18, Eqn. 16. The result is $$p^E = R_K^E \underline{R_R^K R_E^K R_A^E} p^I + R_K^E \underline{R_R^K R_E^K} (c_A^E - c_K^E) + R_K^E \underline{c_R^K + c_K^E} \tag{19}$$

Computing Unknown Transformation

To compute $T_K^R$, we transform model marker point $p^A$ into $p^R$ using Eqn. 15. On the other hand, we transform observed 3d point $p^E$ to $p^K$ using Eqn. 6. Eqn. 17 is used to solve $T_R^K$ ($R_R^K$ and $c_R^K$). This is a reorganization of Eqn. 19.

$$\underbrace{(R_K^E)^{-1} p^E - (R_K^E)^{-1} c_K^E}_{p^K} = \underbrace{R_R^K (R_E^K R_A^E p^I + R_E^K (c_A^E - c_K^E))}_{p^R} + c_R^K \tag{20}$$

The above is the solution of rigid transformation ($p^K$ and $p^R$ known).

The above equations use rotation matrices. Unit quaternion is another rotation parameterization which has advantageous properties for estimation. Eqn. 20 is written as:

$$p^K = q_R^K \otimes p^R \otimes \bar{q}_R^K + c_R^K \tag{21}$$

where $q_K^R$ an equivalent rotation in quaternion form as $R_K^R$ and $\otimes$ represents quaternion multiplication. Note that in the computation of $p^K$ and $p^R$ we do not have to use quaternion.

Correction of a 3d Point Derived Using Kin API

First use Eqn. 6 to transform the coordinates in ECS to KCS. Use Eqn. 17 to compensate and Eqn. 5 to go back to ECS.

$$p^{E'} = T_K^E T_R^K (T_K^E)^{-1} p^E \tag{22}$$

Correction of Remote Center $$p^E = \underbrace{R_K^E R_R^K}_{R_R^E} p^R + \underbrace{R_K^E c_R^K + c_K^E}_{c_R^E} \tag{23}$$

Replacing $\{R_K^E, c_K^E\}$ with $\{R_R^E, c_R^E\}$ when applying the forward kinematics will give the corrected poses for all the segments.

Image Projection

The 3d point $p^E$ is projected into the left image and the right image through two projection processes.

$$u^L = P_L(p^E) \tag{24}$$

$$u^R = P_R(p^E) \tag{25}$$

where $u^L = [u^L, v^L]^T$ is the coordinate of the image point in the Left Image Coordinate System and $P_L(\ )$ is the projection function. Similar for $u^R$ and $P_R(\ )$.

$$u^L = \frac{p_{L1} \cdot [p^E; 1]}{p_{L3} \cdot [p^E; 1]} \tag{26}$$

$$v^L = \frac{p_{L2} \cdot [p^E; 1]}{p_{L3} \cdot [p^E; 1]} \tag{27}$$

where $p_{Li}$ is the i-th row of the camera projection matrix $P_L$. Similar for $u^R$ and $v^R$. Note that we do not consider image distortion here and assume that the distortion has been removed.

Figures 11, 12:
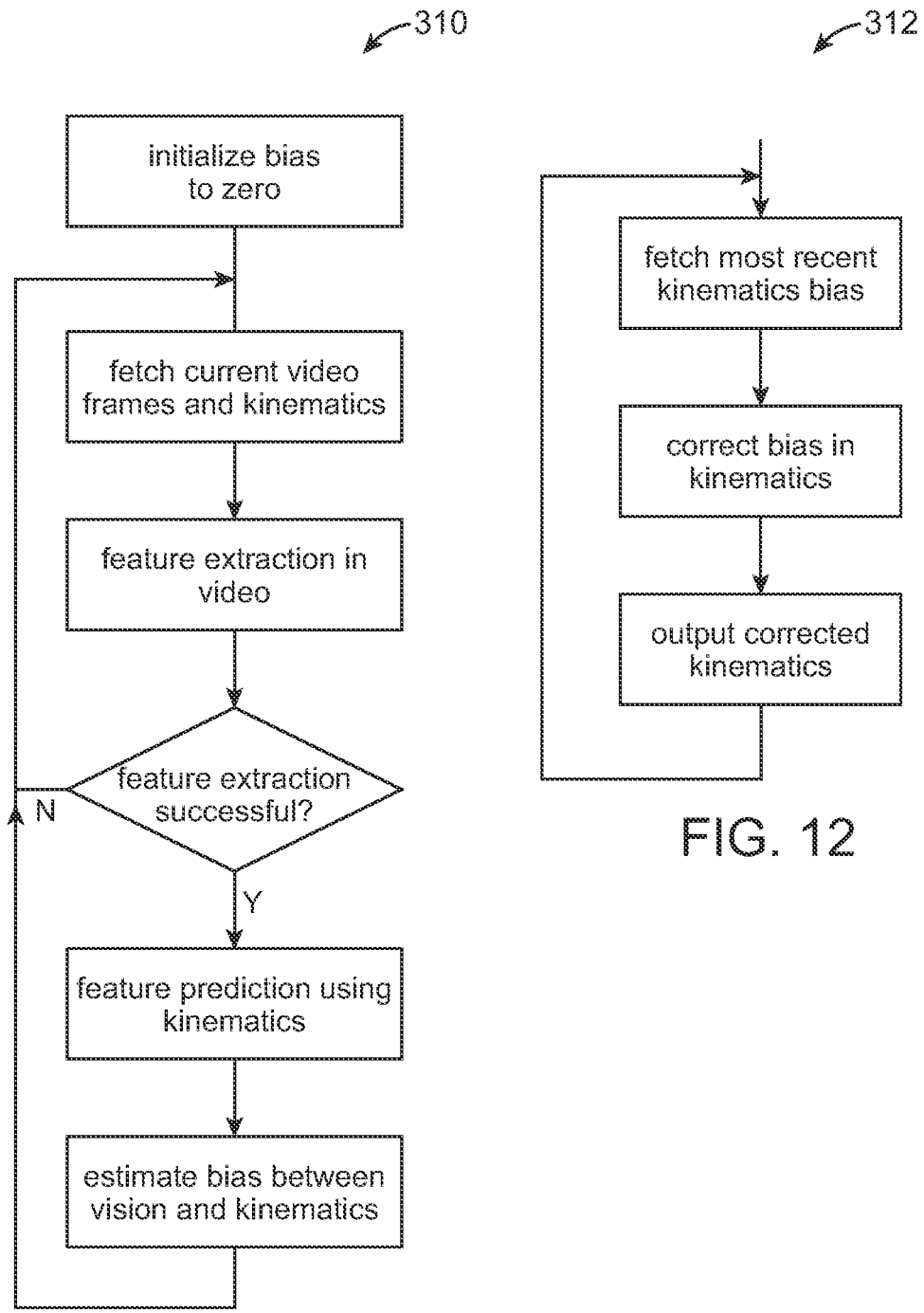
FIG. 11 is a high level flow chart schematically illustrating steps for robotically tracking tools so as to provide more accurate position and/or orientation information.
FIG. 12 is a high level flow chart schematically illustrating processing of the corrected tool tracking information so as to enhance kinematic modeling of the robotic system.
Figure 13:
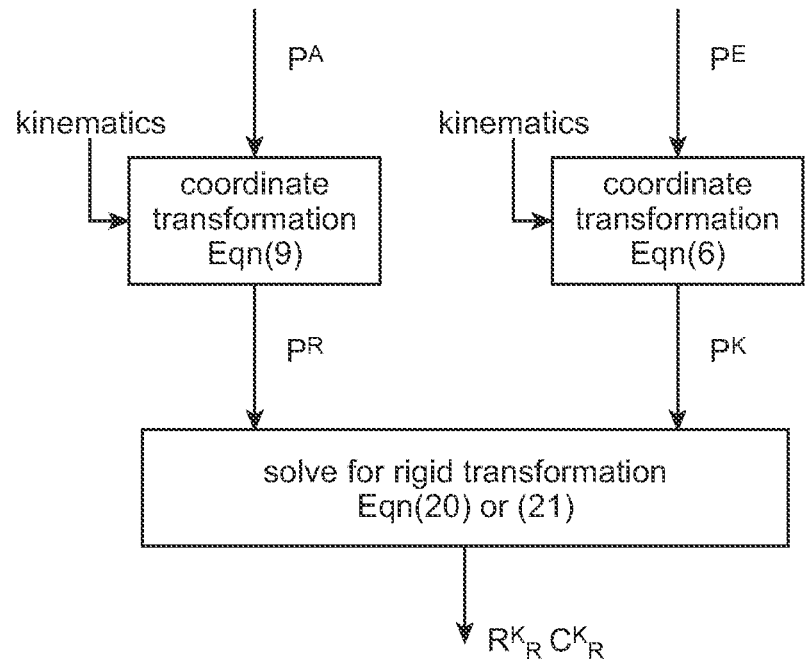
FIG. 13 is a functional block diagram for a three-dimensional point-based fusion module for combining joint-based kinematic data with image-based data.

FIGS. 11 and 12 give top level flowcharts of a tool tracking system, with FIG. 11 presenting the processing thread 310 and FIG. 12 presenting the processing thread 312. FIG. 13 shows the block diagram of the fusion module using 3d-point inputs. To solve for rigid transformation between $p^R$ and $p^K$, a number of choices exist. First, linear solutions of rigid transformation between two sets of 3d points might be used. The advantages of this approach includes the fact that they are computationally efficient. The disadvantage is that it does not easily take consideration of uncertainty of the input in the form of covariance matrices. Non-linear optimization techniques could also be applied. One can use generic numerical optimization techniques to optimize $$\{R_R^{K*}, c_R^{K*}\} = \text{argmax}_{\{R_R^K, c_R^K\}} \tag{28}$$

$$\prod_i \frac{1}{|\Sigma_i|^{1/2}} \exp\left\{ -\frac{1}{2} (R_R^K * p_i^R + c_R^K - p_i^K)^T \Sigma_i^{-1} (R_R^K * p_i^R + c_R^K - p_i^K) \right\}$$

The advantage of such an optimization is that it can handle the input covariance matrices. Optimization based solutions also have the advantage of being quite flexible, while it may be non-trivial (or may not even be possible) to implement all objective functions using at least some other approaches. The disadvantage is that it is computationally expensive, although increasing processor power may mitigate this issue. Alternative approaches may include performing batch estimation using a sliding window, or the like. However, the complexity in both implementation and computation of such batch estimation may be disadvantageous. For fusing the kinematic or joint-based data with the image-based data, particularly so as to provide real-time, near real-time, or online tool location information useful during surgery, it is particularly advantageous to use a filter. The advantages of filters include that they can run in a recursive fashion and there is no need to store past data. It is also computationally efficient to use filters. Hence, filters may be particularly suitable for online estimation, and may represent the preferred approach. The exemplary filters for combining the image-based data with the kinematic information may include the classic Kalman filter family in light of its simplicity, wide use, and well understood behavior. Furthermore, the Kalman filters may have built-in uncertainty propagation which is advantageous for this application.

Still further additional forms of image data might also be implemented.

Kalman Filter Equations

State Vector

The offset of the remote center pose is represented as the true pose of the remote center in the coordinate system of the remote center derived from kinematics (KCS). The true remote center location in KCS $c_R^K = [c_x, c_y, c_z]^T$, and the rotation in the form of unit quaternion $q_R^K = [q_o, q_x, q_y, q_z]^T$. The vector to be estimated is $x_t = [q_0, q_x, q_y, q_z, c_x, c_y, c_z]^T$. $(q_0, q_x, q_y, q_z)$ is the unit quaternion representation of rotation, and $(c_x, c_y, c_z)$ is the translation.

Process Model

This is a simple static process model:

$$x_t = \begin{bmatrix} 1 & 0 & 0 & 0 & 0 & 0 & 0 \\ 0 & 1 & 0 & 0 & 0 & 0 & 0 \\ 0 & 0 & 1 & 0 & 0 & 0 & 0 \\ 0 & 0 & 0 & 1 & 0 & 0 & 0 \\ 0 & 0 & 0 & 0 & 1 & 0 & 0 \\ 0 & 0 & 0 & 0 & 0 & 1 & 0 \\ 0 & 0 & 0 & 0 & 0 & 0 & 1 \end{bmatrix} x_{t-1} + w_{t-1} \quad (33)$$

We assume that it is either fixed or slowly changing, therefore we can model it as a constant process. The process noise can be tuned to find a balance of fast response and stability.

Observation Models

The observations represent image-based data suitable for use in correcting joint-based pose data and can be made in different forms, including 3d marker point locations such as observation is a number of feature points in 3d transformed into the KCS. The observation vector is $p_i^K$ for one 3d point. Multiple points can be easily combined using the Information Filter formulation, as described below. The number of the points should be at least 3 (and not collinear) for the system to be fully observable. The measurement vector is $$y_3 = [x_1, y_1, z_1, \ldots x_n, y_n, z_n]^T \quad (34)$$

The observation model can follow equation (21). The quaternion multiplication can be expanded using equation (31). The observation function which transforms state to observation is not linear (quadratic to rotation and linear to translation), so that an extended Kalman filter (EKF) can be used for filtering. In order to apply an EKF, we provide the following Jacobians:

$$J_1 = \frac{\partial p^K}{\partial q_f^K} \quad (35)$$

$$J_2 = \frac{\partial p^K}{\partial c_f^K} = I \quad (36)$$

Its derivation may use quaternion calculus or a Matlab symbolic toolbox. Matlab symbolic toolbox gives the following equation for $J_1$.

$$J_1 = 2 \begin{bmatrix} q_0 i_x - q_z i_y + q_y i_z & q_x i_x + q_y i_y + q_z i_z & q_0 i_z + q_x i_y - q_y i_x & q_0 i_y + q_x i_z - q_z i_x \\ q_0 i_y - q_x i_z + q_z i_x & -q_0 i_z - q_x i_y + q_y i_x & q_x i_x + q_y i_y + q_z i_z & q_0 i_x - q_z i_y + q_y i_z \\ q_0 i_z + q_x i_y - q_y i_x & q_0 i_y - q_x i_z + q_z i_x & -q_0 i_x - q_y i_z + q_z i_y & q_x i_x + q_y i_y + q_z i_z \end{bmatrix} \quad (37)$$

Information filter, a variant of Kalman filter, is used to handle a large and unknown number of measurement points to avoid inversion of large matrices.

The measurements from one frame need not fully determine the solution. Measurements from multiple frames are combined in the information filter. One can use different kinematics transformations $R_K^E$ and $c_K^E$.

The uncertainty (covariance matrices) of the 3d points are computed and provided to the fusion module as input.

The measurement equation is quadratic (thus non-linear) with respect to the rotation and linear with respect to the translation. Therefore the measurement equations can be linearized (extended information filter) and the filter can run more than a single iteration (iterated extended information filter) for one set of measurements to converge.

Alternative observations may comprise $2^{nd}$ marker point location, such as observation of a number of feature points in both 2d images. The number of the points should be at least 3 for the system to be fully observable. The measurement vector is $$y_4 = [u_1^L, v_1^L, u_1^R, v_1^R, \ldots, u_n^L, v_n^L, u_n^R, v_n^R]^T \quad (38)$$

We want to have $$\frac{\partial [u^L, u^R]}{\partial q_f^K} = \frac{\partial [u^L, u^R]}{\partial p^E} \cdot \frac{\partial p^E}{\partial q_f^K} \quad (39)$$

$$\frac{\partial [u^L, u^R]}{\partial c_f^K} = \frac{\partial [u^L, u^R]}{\partial p^E} \cdot \frac{\partial p^E}{\partial c_f^K} \quad (40)$$

where we only need to provide an extra term $$\frac{\partial [u^L, u^R]}{\partial p^E}.$$

This is a Jacobian of the camera projection.

$$u' = p_{11}x + p_{12}y + p_{13}z + p_{14} \quad (41)$$

$$v' = p_{21}x + p_{22}y + p_{23}z + p_{24} \quad (42)$$

$$w' = p_{31}x + p_{32}y + p_{33}z + p_{34} \quad (43)$$

$$J_{p \to u} = \left(\frac{1}{w'^2}\right) \begin{bmatrix} p_{11}w' - p_{31}u' & p_{12}w' - p_{32}u' & p_{13}w' - p_{33}u' \\ p_{21}w' - p_{31}v' & p_{22}w' - p_{32}v' & p_{23}w' - p_{33}v' \end{bmatrix} \quad (44)$$

where $p_{ij}$ is the i-th row j-th column element of matrix P.

The Effect of Remote Center Motion

The exemplary embodiment relies on a substantially fixed bias of the remote center pose. This holds when the remote center does not move, which is generally the case for real surgical procedures. However there exist situations in which movement of the remote center does occur during surgery. Still, the system converges to the new remote center offset fairly quickly when the move is not too drastic. It is possible that such moves can be compensated through kinematics by properly choosing a coordinate system for the remote center offset. The exemplary embodiment employs the remote center coordinate system. The offset might, for example, be even more stable in the world coordinate system.

3d Line-Based Fusion

Similar to 3d points, two sets of corresponding 3d lines can also be used to compute a rigid transformation. We used the line based technique for tool tracking using the natural instrument appearance. The steps are:

Extract two 2d boundary lines of instrument shaft

Figure 14:
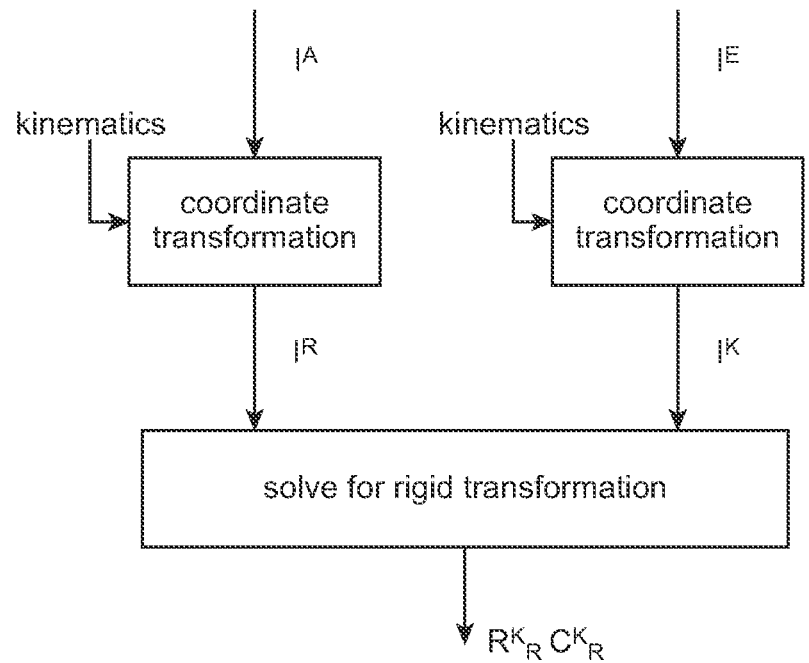
FIG. 14 is a functional block diagram similar to that of FIG. 13, but for combining three-dimensional line-based image data with kinematic data.
Figure 15:
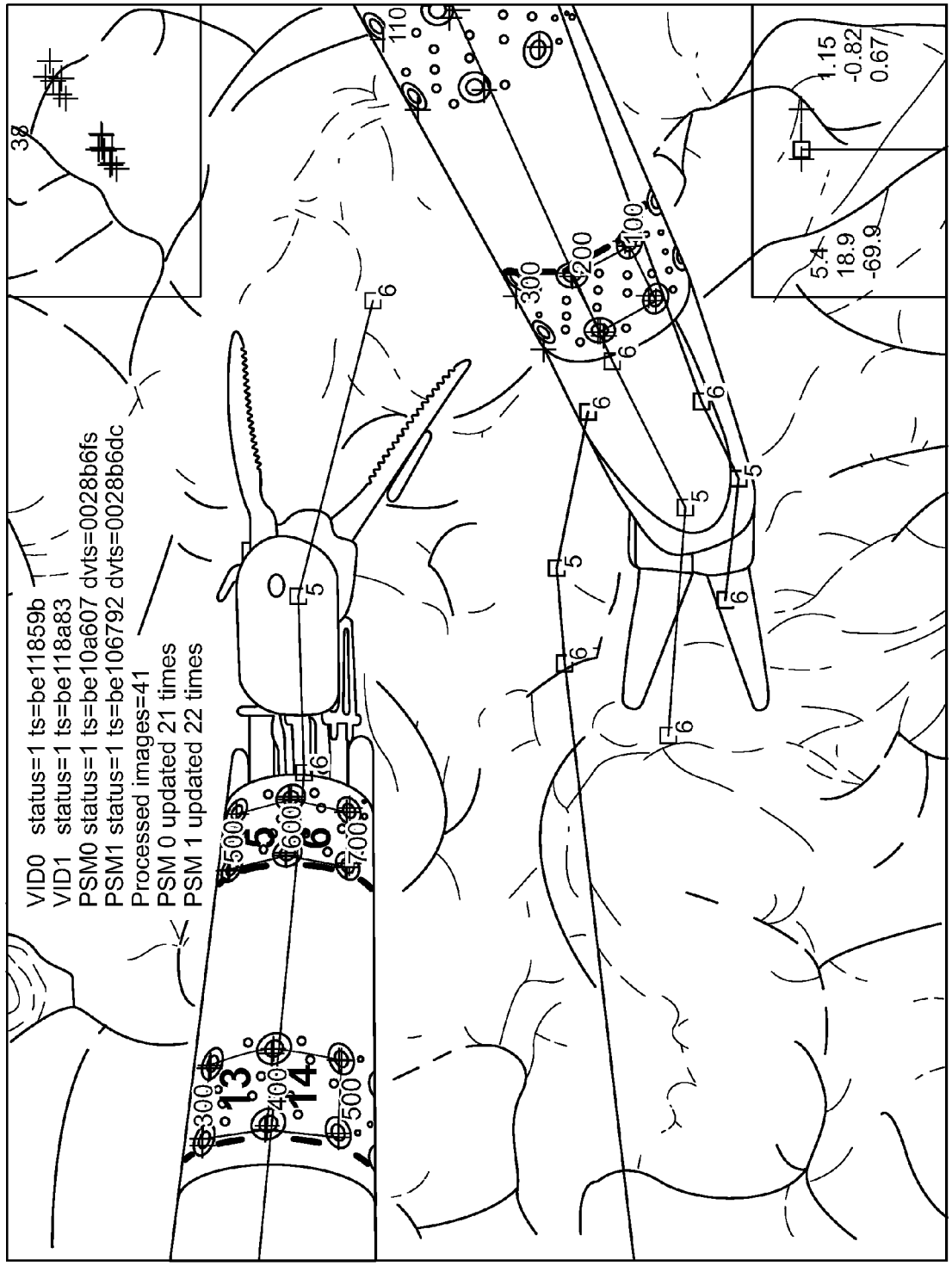
FIG. 15 graphically illustrates output from a fusion of joint-based kinematic data and image-based data for correcting tool position and/or orientational information, with the output of the data fusion superimposed on an image of an internal surgical site showing the robotic surgical tool.

Reconstruct the 3d axis of the cylinder using known camera model and instrument diameter Using the observed 3d axes (from multiple frames) and the corresponding axis from kinematics to solve a rigid transformation between them. The diagram of such a fusion approach is shown in FIG. 14.

Much of the description of the exemplary embodiments above is directed to a particular application of improved image/joint data fusion approaches. Advantageously, many of the systems and techniques described above may have many other uses. Specifically, along with identification of a static bias (such as a rigid transformation) between an image-based pivotal center and a kinematic or joint-based pivotal center (where the bias can be applied as a simple correction for tool tracking, etc) fusion of image-based information and joint-based information could also be applied to other joints or locations along the kinematic chain so as to provide more precise and/or more robust tool pose data. One specific example of an alternative application may be an ultrasound imaging tool for which image data could be used to overcome an unusual amount of joint hysteresis and/or an unidentified manufacturing tolerance error in a tool joint or link. Image based data regarding the tool could be fused with the kinematic data, so as to generate a variable bias (optionally in the form of a look-up table) for correcting the kinematic pose. The look up table may provide differing offsets for differing sets of joint states or tool poses, with interpolation used between discrete table entries, empirical offset functions being derived from the table, or the like. This variable bias information could then be used to increase the positioning accuracy of any ultrasound or other images superimposed on the user display, the accuracy of measurements acquired with the tool tip, etc. Similar enhancements could be made for other applications.

In applying the techniques described above to other joints or links along the kinematic chain, the instrument may be equipped with multiple marker points with the markers optionally being distributed on multiple links of the instrument. The marker placement is known in advance, which is denoted by M.

Vision observations at time t provide the coordinates of the feature points $\tilde{P}^t = \{\tilde{p}_1^t, \ldots, \tilde{p}_n^t\}$, together with their covariance matrices $$\sum\nolimits^t = \left\{ \sum\nolimits_1^t, \ldots, \sum\nolimits_n^t \right\}.$$

Note for simplicity of expression we can assume all the points are visible at any frame, however in practice there is no such restriction.

Kinematics observations provide the remote center T and the active joint angles $\theta_1^t, \ldots, \theta_m^t$. If we assume that the errors of kinematics are constant offsets, dT is the pose offset of the remote center, and $d\theta_1, \ldots, d\theta_m$ are the offsets of the joint angles. The parameters of interest are then $\Theta = \{dT, d\theta_1, \ldots, d\theta_m\}$. Note that these offsets are assumed to be independent of time or to change slowly over time.

$$P^t(\Theta) = F(dT \cdot T, \theta_1^t + d\theta_1, \ldots, \theta_m^t + d\theta_m, M) \quad (45)$$

where F( ) is the vision observation function which includes primarily forward kinematics of the instrument kinematic chain, optionally being camera projection in the case of 2d measurement. The parameters can be estimated from one or more image frames by computing the maximum likelihood (ML) estimation.

$$\Theta^* = \operatorname{argmax} \prod_{t=1}^{T} \prod_{i=1}^{n} \frac{1}{\left(\sum_{i}^{t}\right)^{1/2}} \exp\left\{-\frac{1}{2}(p_i^t(\Theta)\tilde{p}_i^t)\left(\sum_{i}^{t}\right)^{-1}(p_i^t(\Theta) - \tilde{p}_i^t)^T\right\} \quad (46)$$

Note that not all the joint parameters are necessarily observable. For example, if the joint is collocated with the pivotal center, then their offsets may not be separated from that of the pivotal center. This should be determined by the structure of the kinematic chain.

A similar formulation can be generated by assuming that the joint angle errors to be non-linear and in the form of a look-up-tables.

While exemplary embodiments have been described in some detail for clarity of understanding and by way of example, a variety of modifications, adaptations, and changes will be obvious to those of skill in the art. Hence, the scope of the present invention is limited solely by the appended claims.

What is claimed is:

1. A robotic-method for performing surgery on a patient through a minimally invasive aperture, the method comprising:
    positioning, by a robotic surgical system, an elongate shaft of a tool through the minimally invasive aperture so that the shaft pivots at an actual pivotal center adjacent the minimally invasive aperture;
    acquiring, by an image capture device, an image of a surgical site within the patient, the surgical site image including an image of a distal portion of the tool within the field of view of the image capture device, the image of the distal portion including an image of markers, the image capture device being inserted into the patient;
    determining, by the robotic surgical system using the image of the markers, an image-based location of the actual pivotal center;
    determining image-based pivotal center correction information using the image-based location of the actual pivotal center; and
    determining, by the robotic surgical system, a position and/or orientation of the tool by imposing the image-based pivotal center correction information onto joint-based data, the joint-based data being used by a command module to calculate movements of a tool manipulator supporting the tool.

2. The robotic method of claim 1:
    wherein the determining the image-based pivotal center correction information comprises determining a bias offset between a joint-based location of the actual pivotal center per the joint data from the manipulator and the image-based location of the actual pivotal center, and
    wherein the determining the position and/or orientation of the tool comprises adjusting the joint-based pivotal center location per the bias offset such that the image-based location of the actual pivotal center substantially replaces the joint-based location of the actual pivotal center.

3. The robotic method of claim 2:
    wherein the determining the bias offset further comprises determining a bias offset between a joint-based pivotal center pose defined by the joint-based location of the actual pivotal center and an orientation of the shaft per joint data from the manipulator, and an image-based pivotal center pose defined by the image-based location of the actual pivotal center and an orientation of the shaft per the image, and wherein the determining the position and/or orientation of the tool further comprises adjusting the joint-based pivotal center pose per the bias offset such that the image-based pivotal center pose substantially replaces the joint-based pivotal center pose, and such that other poses along a linkage of the tool and the tool manipulator are calculated using joint-based data.

4. The robotic method of claim 3:

wherein the determining the bias offset further comprises determining a rigid transformation between the joint-based pivotal center pose and the image-based pivotal center pose, and wherein the robotic method further comprises applying, by the command module, the rigid transformation to the joint-based pivotal center pose.

5. The robotic method of claim 3:

wherein the image capture device is movably supported by a camera manipulator of the robotic surgical system, wherein the determining the bias offset further comprises:
 determining the image-based pivotal center pose using a camera coordinate system of the image capture device,
 generating, by the command module, the joint-based pivotal center pose in response to joint states of the tool and the tool manipulator,
 determining, by the command module, a joint-based camera coordinate system, and wherein the determined bias offset is determined between the joint-based location of the actual pivotal center in the joint-based camera coordinate system and the image-based location of the actual pivotal center in the camera coordinate system.

6. The robotic method of claim 5:

wherein the camera manipulator is supported by a movable camera support of the robotic surgical system, wherein the tool manipulator is supported by a movable tool support of the robotic surgical system, wherein the robotic method further comprises pivoting, by the tool manipulator, the shaft during the movements at the actual pivotal center about a pitch axis and about a yaw axis, and wherein the bias offset comprises a combination of:
 tool support data error;
 camera support data error;
 pitch data error; and
 yaw data error.

7. The robotic method of claim 6:

wherein the tool support comprises a tool set-up linkage and the tool support data error comprises joint state data error and structural inaccuracy of the tool set-up linkage, and wherein the camera support comprises a set-up linkage and the tool support data error comprises joint state data error and structural inaccuracy of the camera set-up linkage.

8. The robotic method of claim 1:

wherein a plurality of images is obtained by a plurality of angularly offset image capture devices of the robotic surgical system, the plurality of offset image capture devices including the image capture device, wherein the robotic method further comprises determining a three-dimensional (3D) image-based pivotal center pose using the plurality of images, and wherein the image-based pivotal center pose comprises an image-based 3D orientation along the shaft and an image-based location of the actual pivotal center in three dimensions.

9. The robotic method of claim 8:

wherein the plurality of images comprises a time-series of images, and wherein the robotic method further comprises obtaining, for each image in the time-series of images, associated joint-based data synchronized with the image, and computing the image based pivotal center pose using the time series of images and the associated joint-based data.

10. The robotic method of claim 9, further comprising determining a time series of tool locations from the time-series of images, detecting any outlier tool location, and removing any detected outlier before computing the image based pivotal center pose.

11. The robotic method of claim 9, further comprising determining a region of interest of a first image of the time-series based on a location of the tool in at least one prior second image of the time-series, wherein the location of the tool in the first image is determined by processing the portion of the first image within the region of interest.

12. The robotic method of claim 8, further comprising:
 determining, by the command module, a joint-based pivotal center pose using joint data from the tool manipulator,
 wherein the determining the image-based pivotal center pose comprises determining an image-based location of the actual pivotal center using image pairs of the plurality of images from the plurality of angularly offset image capture devices, and
 wherein the determining the position and/or orientation of the tool comprises solving for a rigid transformation between the image-based pivotal center pose and the joint-based pivotal center pose using a recursive filter.

13. The robotic method of claim 12, wherein the determining the image-based pivotal center pose comprises identifying a plurality of marker points along the tool from the plurality of images.

14. The robotic method of claim 12, wherein the determining the image-based pivotal center pose comprises identifying at least one structural location line along the tool from the plurality of images.

15. A robotic method for performing surgery on a patient through a minimally invasive aperture with a robotic system, the robotic system including a tool having an elongate shaft and a command module that determines movements of a tool manipulator supporting the tool by determining a joint-based pivotal center pose of the tool, the method comprising:
 positioning, by the robotic system, the elongate shaft of the tool through the minimally invasive aperture so that the shaft pivots at an actual pivotal center adjacent the minimally invasive aperture, the actual pivotal center and the shaft defining an actual pivotal center pose;
 acquiring, by an image capture device of the robotic system, an image of a surgical site within the patient, the surgical site image including an image of a distal portion of the tool within the field of view of the image capture device, the image of the distal portion of the tool including an image of markers, the image capture device being inserted into the patient;

determining, by the robotic system using the image of the markers, an image-based pose of the actual pivotal center pose;

calculating, by the robotic system, a rigid transformation between the image-based pose of the actual pivotal center pose and the joint-based pivotal center pose using a recursive filter; and determining, by the robotic system, a location and/or orientation of the tool by using the rigid transformation to mitigate an error between the joint-based pivotal center pose and the actual pivotal center pose.

16. A robotic method for use with a robotic system including a manipulator movably supporting a tool and a command module generating movement commands of the manipulator so as to generate desired movements of the tool based on joint data from the manipulator, wherein environmental constraints induce an error in a joint-based pivotal center pose of the tool, the joint-based pivotal center pose being calculated by the command module along a linkage of the manipulator or tool, the joint-based pivotal center pose being defined by a joint-based location of an actual pivotal center and an orientation of a shaft of the tool per joint data, the shaft of the tool entering the patient through an incision in a patient, the shaft pivoting at the actual pivotal center, the actual pivotal center being adjacent the incision, the method comprising:

acquiring, by the robotic system, an image of a surgical site within the patient, the surgical site image including an image of a distal portion of the tool within the field of view of the image capture device, the image of the distal portion of the tool including an image of markers, the image capture device being inserted into the patient selectively determining, by the robotic system using the image of the markers, an image-based pivotal center pose of the tool reflecting the environmental constraints, the image-based pivotal center pose of the tool being defined by an image-based location of the actual pivotal center and an orientation of the shaft per the image of the distal portion of the tool;

calculating, by the robotic system, a rigid transformation between the image-based pivotal center pose and the joint-based pivotal center pose; and determining, by the robotic system, a location of the actual pivotal center and orientation of the shaft of the tool by using the rigid transformation so as to mitigate the error in the joint-based pivotal center pose of the tool induced by the environmental constraints.

17. The robotic method of claim 16, wherein calculating the rigid transformation comprises using a recursive filter with a series of image-based pivotal center poses and an associated series of calculated joint-based pivotal center poses.

18. The robotic method of claim 17, further comprising updating the rigid transformation.

19. A robotic system for performing surgery on a patient through a minimally invasive aperture, the system comprising:

a tool having a proximal end, a distal end, and an elongate shaft, the distal end of the tool being configured to be insertable through the minimally invasive aperture, the distal end of the tool including markers, and the shaft being configured to pivot at a pivotal center adjacent the minimally invasive aperture;

an image capture device, the image capture device being configured to be insertable in the patent, the image capture device being configured to acquire an image of a surgical site within the patient, the surgical site image including an image of a distal end of the tool within the field of view of the image capture device, the image of the distal end of the tool including an image of markers;

a tool manipulator supporting the proximal end of the tool; and a processor system coupling the image capture device to the tool manipulator, the processor system including a tool correction module and a command module, the command module being coupled to the tool manipulator, the command module being configured to transmit tool movement commands to the tool manipulator, the command module being configured to calculate a joint-based pivotal center in response to joint signals from the tool manipulator, the tool correction module being configured to generate a corrected tool position and/or orientation by determining an image-based location of the pivotal center using the image of the markers, by determining image-based pivotal center correction information using the image-based location of the pivotal center, and by correcting the joint-based pivotal center with the image-based pivotal center correction information.

20. A correction system comprising:

a tool correction module coupling an image capture device of a robotic surgical system to a command module of the robotic surgical system, the robotic surgical system comprising a tool having a proximal end, a distal end, and an elongate shaft, the distal end of the tool being configured to be insertable through a minimally invasive aperture in a patient, the distal end of the tool including markers, and the shaft being configured to pivot at a pivotal center adjacent the minimally invasive aperture; the image capture device being configured to be insertable in the patent and the image capture device being configured to acquire an image of a surgical site within the patient, the surgical site image including an image of a distal end of the tool within the field of view of the image capture device, the image of the distal end of the tool including an image of markers; a tool manipulator supporting the proximal end of the tool; and a processor system including the command module coupled to the tool manipulator, the command module being configured to transmit tool movement commands to the tool manipulator, and the command module being configured to calculate a joint-based location of the pivotal center in response to joint signals; and the tool correction module being configured to determine a position and/or orientation of the tool by determining an image-based location of the pivotal center using the image of the markers, by determining image-based pivotal center correction information using the image-based location of the pivotal center, and by correcting the joint-based location of the pivotal center with the image-based pivotal center correction information such that an error between the joint-based pivotal center and the actual pivotal center is mitigated.

21. The correction system of claim 20, wherein the tool correction module is configured to determine a bias offset between a joint-based location of the pivotal center per the joint signals from the tool manipulator, and the image-based location of the pivotal center per the image.

22. The correction system of claim 21, wherein the tool correction module is configured to determine the bias offset by determining an offset between a joint-based pivotal center pose defined by the location of the joint-based location of the pivotal center and an orientation of the shaft per the joint signals from the tool manipulator, and an image-based pivotal center pose defined by the image-based location of the pivotal center and an orientation of the shaft per the image.

23. The correction system of claim 22, wherein the tool correction module is configured to determine the bias offset by determining a rigid transformation between the joint-based pivotal center pose and the image-based pivotal center pose.

24. The correction system of claim 23, the robotic system including a camera manipulator movably supporting the image capture device, the command module of the robotic system generating the joint-based pivotal center pose in response to joint states of the tool and the tool manipulator and also determining a joint-based camera coordinate system, wherein the tool correction module is configured to determine the image-based pivotal center pose using a camera coordinate system of the image capture device, and wherein the tool correction module is configured to determine the bias offset between the joint-based location of the pivotal center in the joint-based camera coordinate system and the image-based location of the pivotal center in the camera coordinate system.

25. The correction system of claim 20, the robotic system comprising a plurality of angularly offset image capture devices configured to acquire a plurality of images, the plurality of angularly offset image capture devices including the image capture device, wherein the tool correction module is configured for determining a three-dimensional (3D) image-based pivotal center pose using the plurality of images, the image-based pivotal center pose comprising an image-based 3D orientation along the shaft and an image-based location of the pivotal center in three dimensions.

26. The correction system of claim 25, the command module determining a joint-based pivotal center pose using joint data from the tool manipulator, wherein the tool correction command module is configured for determining the image-based location of the pivotal center from of image pairs of the plurality of images transmitted from the plurality of angularly offset image capture devices, and wherein the tool correction module comprises a recursive filter that determines the pivotal center pose by solving for a rigid transformation between the image-based pivotal center pose and the joint-based pivotal center pose.

27. The correction system of claim 26, wherein the tool correction module determines the image-based pivotal center pose is by identifying a plurality of marker points along the tool from the plurality of images.

28. The correction system of claim 26, wherein the tool correction module determines the image-base pivotal center pose by identifying at least one structural location line along the tool from the plurality of images.

29. A robotic system comprising:
a manipulator movably supporting a tool having an elongate shaft;
a command module generating movement commands of the manipulator so as to generate desired movements of the tool based on joint data from the manipulator, wherein environmental constraints induce an error in a joint-based pivotal center pose calculated by the command module along a linkage of the manipulator or tool, the joint-based pivotal center pose being defined by a joint-based location of an actual pivotal center and an orientation of a shaft of the tool per joint data, the shaft of the tool entering the patient through an incision in a patient, the shaft pivoting at the actual pivotal center, the actual pivotal center being adjacent the incision;
an image capture device for acquiring an image of a surgical site within the patient, the surgical site image including an image of a distal portion of the tool within the field of view of the image capture device, the image of the distal portion of the tool including an image of markers, if the image capture device is inserted into the patient;
means for image-based correction coupling the image capture device to the command module, the correction means comprising means for determining an image-based pivotal center pose of the tool from the image of the markers, the image-based pivotal center pose reflecting the environmental constraints, the image-based pivotal center pose of the tool being defined by the image-based pivotal center location and an orientation of the shaft per the image of the distal portion of the tool, means for calculating a rigid transformation between the image based pivotal center pose of the tool and the joint-based pivotal center pose, and means for using the rigid transformation to mitigate the error in the joint-based pivotal center pose of the tool induced by the environmental constraints.

30. The robotic system of claim 29, wherein the means for correcting comprises a recursive filter.

31. The robotic system of claim 29, wherein the command module does not apply the image-based pose for calculating the movement commands.

32. The robotic system of claim 29, wherein the command module comprises means for applying the rigid transformation to calculate the movement commands.

* * * * *